United States Patent
Eaton et al.

(10) Patent No.: US 6,660,256 B1
(45) Date of Patent: Dec. 9, 2003

(54) PORCINE MPL LIGAND

(75) Inventors: Dan L. Eaton, San Rafael, CA (US); Frederic J. de Sauvage, Foster City, CA (US)

(73) Assignee: Genetech, Inc., South San Francisco, CA (US)

(*) Notice: Subject to any disclaimer, the term of this patent is extended or adjusted under 35 U.S.C. 154(b) by 0 days.

(21) Appl. No.: 08/348,657

(22) Filed: Dec. 2, 1994

Related U.S. Application Data

(63) Continuation of application No. 08/176,553, filed on Jan. 3, 1994, now abandoned.

(51) Int. Cl.$^7$ .............................................. A61K 38/19

(52) U.S. Cl. .......................... 424/85.1; 514/2; 514/12; 530/350; 530/351

(58) Field of Search ................................ 530/351, 350, 530/387.1; 514/2, 12; 424/85.1; 435/69.7, 69.1

(56) References Cited

U.S. PATENT DOCUMENTS

| | | | | |
|---|---|---|---|---|
| 4,894,440 A | * | 1/1990 | Rosenberg | 530/351 |
| 5,223,408 A | | 6/1993 | Goeddel et al. | 435/69.3 |
| 5,260,417 A | * | 11/1993 | Grant et al. | 530/351 |
| 5,326,558 A | * | 7/1994 | Turner et al. | 424/85.1 |

FOREIGN PATENT DOCUMENTS

| | | |
|---|---|---|
| WO | WO 90/12877 | 11/1990 |
| WO | WO 93/11247 | 6/1993 |

OTHER PUBLICATIONS

N. Methia et al., Blood 82(5):1395–1401, Sep. 1, 1993.*
R.C. Skolda et al., EMBO J. 12(7):2645–2653, 1993.*
de Sauvage et al. Nature 369:533, 1994.*
McDonald, "Thrombopoietin: Its Biology, Clinical Aspects, and Possibilities" *The American Journal of Pediatric Hematology/Oncology* 14(1):8–21 (1992).
McDonald et al., "Monoclonal Antibodies to Human Urinary Thrombopoietin" *Proc. Soc. Exp. Biol. Med.* 182:151–158 (1986).
Bartley et al., "Identification and Cloning of a Megakaryocyte Growth and Development Factor That Is a Ligand for the Cytokine Receptor Mpl" *Cell* 77:1117–1124 (1994).
Bazan, "Structural design and molecular evolution of a cytokine receptor superfamily" *Proc. Natl. Acad. Sci. USA* 87:6934–6938 (1990).
Davis et al., "The Receptor for Ciliary Neurotrophic Factor" *Science* 253:59–63 (1991).
Foster et al., "Human thrombopoietin: Gene structure, cDNA sequence, expression, and chromosomal localization" *Proc. Natl. Acad. Sci. USA* 91(26):13023–13027 (1994).

Gearing et al., "Expression cloning of a receptor for human granulocyte–macrophage colony–stimulating factor" *EMBO Journal* 8(12):3667–3676 (1989).
Hill et al., "The Effect of Partially Purified Thrombopoietin on Guinea Pig Megakaryocyte Ploidy in vitro" *Experimental Hematology* 17(8):903–907 (1989).
Hoffman, "Regulation of Megakaryocytopoiesis" *Blood* 74(4):1196–1212 (1989).
Hunt et al., "Purification and Biologic Characterization of Plasma–Derived Megakaryocyte Growth and Development Factor" *Blood* 86(2):540–547 (1995).
Kaushansky, "Thrombopoietin: The Primary Regulator of Platelet Production" *Blood* 86(2):419–431 (1995).
Kellar et al., "Thrombopoietin–induced stimulation of megakaryocyte–enriched bone marrow cultures" *Int. Cong. Throm. Haem.* (Abstract P5–028/0668) 42(1):283 (1979).
Lok et al., "Cloning and Expression of Murine Thrombopoietin cDNA and Stimulation of Platelet Production In Vivo" *Nature* 369:565–568 (Jun. 16, 1994).
Lok et al., "The Structure, Biology and Potential Therapeutic Applications of Recombinant Thrombopoietin" *Stem Cells* 12(6):586–598 (1994).
McDonald, "Thrombopoietin: Its Biology, Purification, and Characterization" *Experimental Hematology* 16(3):201–205 (1988).
McDonald et al., "A Four–step Procedure for the Purification of Thrombopoietin" *Experimental Hematology* 17(8):865–871 (1989).
McDonald et al., "Purification and Assay of Thrombopoietin" *Experimental Hematology* 2(6):355–361 (1974).
McDonald et al., "Studies on the purification of thrombopoietin from kidney cell culture medium" *Journal of Laboratory and Clinical Medicine* 106(2):162–174 (1985).
Metcalf, "Thrombopoietin—at last" *Nature* 369:519–520 (1994).
Nicola et al., "Subunit Promiscuity among Hemopoietic Growth Factor Receptors" *Cell* 67:1–4 (1991).
Sohma et al., "Molecular cloning and chromosomal localization of the human thrombopoietin gene" *FEBS Letters* 353(1):57–61 (1994).

(List continued on next page.)

Primary Examiner—Lorraine Spector
(74) Attorney, Agent, or Firm—Timothy R. Schwartz

(57) ABSTRACT

Isolated mpl ligand, isolated DNA encoding mpl ligand, and recombinant methods of preparing mpl ligand are disclosed. These mpl ligands are shown to influence the replication, differentiation or maturation of blood cells, especially megakaryocyte progenitor cells. Accordingly, these compounds are used for treatment of thrombocytopenia.

3 Claims, 6 Drawing Sheets

OTHER PUBLICATIONS

Souyri et al., "A Putative Truncated Cytokine Receptor Gene Transduced by the Myeloproliferative Leukemia Virus Immortalizes Hematopoietic Progenitors" *Cell* 63:1137–1147 (1990).

Vigon et al., "Characterization of the murine Mpl proto-oncogene, a member of the hematopoietic cytokine receptor family: molecular cloning, chromosomal location and evidence for a function in cell growth" *Oncogene* 8:2607–2615 (1993).

Vigon et al., "Expression of the c–mpl Proto–oncogene in Human Hematologic Malignancies" *Blood* 82(3):877–883 (1993).

Vigon et al., "Molecular cloning and characterization of MPL, the human homolog of the v–mpl oncogene: Identification of a member of the hematopoietic growth factor receptor superfamily" *Proc. Natl. Acad. Sci. USA* 89:5640–5644 (1992).

* cited by examiner

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 20 amino acids
      (B) TYPE: Amino Acid
      (D) TOPOLOGY: Linear (xi) SEQUENCE DESCRIPTION: SEQ ID NO:1:

```
Ser Pro Ala Pro Pro Ala Cys Asp Pro Arg Leu Leu Asn Lys Leu
 1               5                  10                  15

Leu Arg Asp Asp His
                20
```

(2) INFORMATION FOR SEQ ID NO:2:

(i) SEQUENCE CHARACTERISTICS:
      (A) LENGTH: 25 amino acids
      (B) TYPE: Amino Acid
      (D) TOPOLOGY: Linear (xi) SEQUENCE DESCRIPTION: SEQ ID NO:2:

```
Ser Pro Ala Pro Pro Ala Cys Asp Pro Arg Leu Leu Asn Lys Leu
 1               5                  10                  15

Leu Arg Asp Asp His Val Leu His Gly Arg
                20                  25
```

(2) INFORMATION FOR SEQ ID NO:3:

(i) SEQUENCE CHARACTERISTICS:
      (A) LENGTH: 26 amino acids
      (B) TYPE: Amino Acid
      (D) TOPOLOGY: Linear (xi) SEQUENCE DESCRIPTION: SEQ ID NO:3:

```
Ser Pro Ala Pro Pro Ala Cys Asp Pro Arg Leu Leu Asn Lys Leu
 1               5                  10                  15

Leu Arg Asp Asp Xaa Val Leu His Gly Arg Leu
                20                  25  26
```

(2) INFORMATION FOR SEQ ID NO:4:

(i) SEQUENCE CHARACTERISTICS:
      (A) LENGTH: 25 amino acids
      (B) TYPE: Amino Acid
      (D) TOPOLOGY: Linear (xi) SEQUENCE DESCRIPTION: SEQ ID NO:4:

```
Ser Pro Ala Pro Pro Ala Xaa Asp Pro Arg Leu Leu Asn Lys Leu
 1               5                  10                  15

Leu Arg Asp Asp His Val Leu His Gly Arg
                20                  25
```

(2) INFORMATION FOR SEQ ID NO:5:

(i) SEQUENCE CHARACTERISTICS:
      (A) LENGTH: 14 amino acids
      (B) TYPE: Amino Acid
      (D) TOPOLOGY: Linear (xi) SEQUENCE DESCRIPTION: SEQ ID NO:5:

Xaa Pro Ala Pro Pro Ala Xaa Asp Pro Arg Leu Xaa Asn Lys
  1               5                  10                  14

(2) INFORMATION FOR SEQ ID NO:6:

(i) SEQUENCE CHARACTERISTICS:
        (A) LENGTH: 20 base pairs
        (B) TYPE: Nucleic Acid
        (C) STRANDEDNESS: Single
        (D) TOPOLOGY: Linear (xi) SEQUENCE DESCRIPTION: SEQ ID NO:6:

CCNGCNCCNC CNGCNTGYGA                                           20

(2) INFORMATION FOR SEQ ID NO:7:

(i) SEQUENCE CHARACTERISTICS:
        (A) LENGTH: 21 base pairs
        (B) TYPE: Nucleic Acid
        (C) STRANDEDNESS: Single
        (D) TOPOLOGY: Linear (xi) SEQUENCE DESCRIPTION: SEQ ID NO:7:

NCCRTGNARN ACRTGRTCRT C                                         21

(2) INFORMATION FOR SEQ ID NO:8:

(i) SEQUENCE CHARACTERISTICS:
        (A) LENGTH: 69 base pairs
        (B) TYPE: Nucleic Acid
        (C) STRANDEDNESS: Double
        (D) TOPOLOGY: Linear (xi) SEQUENCE DESCRIPTION: SEQ ID NO:8:

CCAGCGCCGC CAGCCTGTGA CCCCCGACTC CTAAATAAAC TGCCTCGTGA          50

TGACCACGTT CAGCACGGC                                            69

(2) INFORMATION FOR SEQ ID NO:9:

(i) SEQUENCE CHARACTERISTICS:
        (A) LENGTH: 69 base pairs
        (B) TYPE: Nucleic Acid
        (C) STRANDEDNESS: Double
        (D) TOPOLOGY: Linear (xi) SEQUENCE DESCRIPTION: SEQ ID NO:9:

CCAGCACCTC CGGCATGTGA CCCCCGACTC CTAAATAAAC TGCTTCGTGA          50

CGACCACGTC CATCACGGC                                            69

(2) INFORMATION FOR SEQ ID NO:10:

(i) SEQUENCE CHARACTERISTICS:
        (A) LENGTH: 9 amino acids
        (B) TYPE: Amino Acid
        (D) TOPOLOGY: Linear (xi) SEQUENCE DESCRIPTION: SEQ ID NO:10:

Pro Arg Leu Leu Asn Lys Leu Leu Arg
  1               5                  9

(2) INFORMATION FOR SEQ ID NO:11:

(i) SEQUENCE CHARACTERISTICS:
        (A) LENGTH: 69 base pairs

-continued

```
        (B) TYPE: Nucleic Acid
        (C) STRANDEDNESS: Double
        (D) TOPOLOGY: Linear (xi) SEQUENCE DESCRIPTION: SEQ ID NO:11:

CCAGCACCGC CGGCATGTGA CCCCCGACTC CTAAATAAAC TGCTTCGTGA          50

CGATCATGTC TATCACGGT                                            69

(2) INFORMATION FOR SEQ ID NO:12:

(i) SEQUENCE CHARACTERISTICS:
        (A) LENGTH: 53 base pairs
        (B) TYPE: Nucleic Acid
        (C) STRANDEDNESS: Single
        (D) TOPOLOGY: Linear (xi) SEQUENCE DESCRIPTION: SEQ ID NO:12:

CCAGCACCGC CGGCATGTGA CCCCCGACTC CTAAATAAAC TGCTTCGTGA          50

CGA                                                             53
```

PORCINE MPL LIGAND

CROSS REFERENCE

This application is a continuation of earlier filed U.S. application Ser. No. 08/176,553 filed Jan. 3, 1994 abandoned, which application is incorporated herein by reference and to which application priority is claimed under 35 USC §120.

FIELD OF THE INVENTION

This invention relates to the isolation, purification and characterization of proteins that influence the replication, differentiation or maturation of blood cells, especially platelet progenitor cells. This invention further relates to the cloning and expression of a protein ligand capable of binding to and activating mpl, a member of the cytokine receptor superfamily. This application further relates to the use of these proteins alone or in combination with other cytokines to treat thrombocytopenia.

BACKGROUND OF THE INVENTION

I. Megakaryocytopoiesis

It is known that bone marrow pluripotent stem cells differentiate into megakaryocytic, erythrocytic, and myelocytic cell lines. It is believed there is also a line of committed cells between stem cells and megakaryocytes. The earliest recognizable member of the megakaryocyte (meg) family are the megakaryoblasts. These cells are initially 20 to 30 $\mu$m in diameter having basophilic cytoplasm and a slightly irregular nucleus with loose, somewhat reticular chromatin and several nucleoli. Later, megakaryoblasts may contain up to 32 nuclei, but the cytoplasm remains sparse and immature. As maturation proceeds, the nucleus becomes more lobulate and pyknotic, the cytoplasm increases in quantity and becomes more acidophilic and granular. The most mature cells of this family may give the appearance of releasing platelets at their periphery. Normally, less than 10% of megakaryocytes are in the blast stage and more than 50% are mature. Arbitrary morphologic classifications commonly applied to the megakaryocyte series: are megakaryoblast for the earliest form; promegakaryocyte or basophilic megakaryocyte for the intermediate form; and mature (acidophilic, granular, or platelet-producing) megakaryocyte for the late forms. The mature megakaryocyte extends filaments of cytoplasm into sinusoidal spaces where they detach and fragment into individual platelets (Williams et al., *Hematology*, 1972).

Megakaryocytopoiesis is believed to involve several regulatory factors (Williams et al., *Br. J. Haematol.*, 52:173 [1982] and Williams et al., *J. Cell Physiol.* 110:101 [1982]). The early level of megakaryocytopoiesis is postulated as being mitotic, concerned with cell proliferation and colony initiation from CFU-meg but is not affected by platelet count (Burstein et al., *J. Cell Physiol.* 109:333 [1981] and Kimura et al., *Exp. Hematol.* 13:1048 [1985]). The later stage of maturation is non-mitotic, involved with nuclear polyploidization and cytoplasmic maturation and is probably regulated in a feedback mechanism by peripheral platelet number (Odell et al., *Blood* 48:765 [1976] and Ebbe et al., *Blood* 32:787 [1968]). The existence of a distinct and specific megakaryocyte colony-stimulating factor (meg-CSF) has been disputed (Mazur, E., *Exp. Hematol.* 15:340–350 [1987]). Although. meg-CSF's have been partly purified from experimentally produced thrombocytopenia (Hill et al., *Exp. Hematol.* 14:752 [1986]) and human embryonic kidney conditioned medium [CM] (McDonald et al., *J. Lab. Clin. Med.* 85:59 [1975]) and in man from aplastic anemia and idiopathic thrombocytopenic purpura urinary extracts (Kawakita et al., *Blood* 6:556 [1983]) and plasma (Hoffman et al., *J. Clin. Invest.* 75:1174 [1985]), their physiological function is as yet unknown in most cases. The conditioned medium of pokeweed mitogen-activated spleen cells (PWM-SpCM) and the murine myelomonocyte cell line WEHI-3 (WEHI-3CM) have been used as megakaryocyte potentiators. PWM-SpCM contains factors enhancing CFU-meg growth (Metcalf et al., *Pro. Natl. Acad. Sci., USA* 72:1744–1748 [1975]; Quesenberry et al., *Blood* 65:214 [1985]; and Iscove, N. N., in *Hematopoietic Cell Differentiation, ICN-UCLA Symposia on Molecular and Cellular Biology*, Vol. 10, Golde et al., eds. [New York, Academy Press] pp 37–52 [1978]), one of which is interleukin-3 (IL-3), a multilineage colony stimulating factor (multi-CSF [Burstein, S. A., *Blood Cells* 11:469 [1986]). The other factors in this medium have not yet been identified and isolated. WEHI-3 is a murine myelomonocytic cell line secreting relatively large amounts of IL-3 and smaller amounts of GM-CSF. IL-3 has been recently purified and cloned (Ihle et al., *J. Immunol.* 129:2431 [1982]) and has been found to potentiate the growth of a wide range of hemopoietic cells (Ihle et al., *J. Immunol.* 13:282 [1983]). IL-3 has also been found to synergize with many of the known hemopoietic hormones or growth factors (Bartelmez et al., *J. Cell Physiol.* 122:362–369 [1985] and Warren et al., *Cell* 46:667–674 [1988]), including both erythropoietin (EPO) and H-1 (later known as interleukin-1 or IL-1), in the induction of very early multipotential precursors and the formation of very large mixed hemopoietic colonies.

Other sources of megakaryocyte potentiators have been found in the conditioned media of murine lung, bone, macrophage cell lines, peritoneal exudate cells and human embryonic kidney cells. Despite certain conflicting data (Mazur, E., *Exp. Hematol.* 15:340–350 [1987]), there is some evidence (Geissler et al., *Br. J. Haematol.* 60:233–238 [1985]) that activated T lymphocytes rather than monocytes play an enhancing role in megakaryocytopoiesis. These findings suggest that activated T-lymphocyte secretions such as interleukins may be regulatory factors in meg development (Geissler et al., *Exp. Hematol.* 15:845–853 [1987]). A number of studies on megakaryocytopoiesis with purified EPO (Vainchenker et al., *Blood* 54:940 [1979]; McLeod et al., *Nature* 261:492–4 [1976]; and Williams et al., *Exp. Hematol.* 12:734 [1984]) indicate that this hormone has an enhancing effect on meg colony formation. More recently this has been demonstrated in both serum-free and serum-containing cultures and in the absence of accessory cells (Williams et al., *Exp. Hematol.* 12:734 [1984]). EPO was postulated to be involved more in the single and two-cell stage aspects of megakaryocytopoiesis as opposed to the effect of PWM-SpCM which was involved in the four-cell stage of megakaryocyte development. The interaction of all these factors on both early and late phases of megakaryocyte development remains to be elucidated.

Other documents of interest include: Eppstein et al., U.S. Pat. No. 4,962,091; Chong, U.S. Pat. No. 4,879,111; Fernandes et al., U.S. Pat. No. 4,604,377; Wissler et al., U.S. Pat. No. 4,512,971; Gottlieb, U.S. Pat. No. 4,468,379; Kogan et al., U.S. Pat. No. 5,250,732; Kimura et al., *Eur. J. Immunol.*, 20(9): 1927–1931 (1990); Secor, W. E. et al., *J. of Immunol.*, 144(4): 1484–1489 (1990); Warren, D. J., et al., *J. of Immunol.* 140(1): 94–99 (1988); Warren, M. K. et al., *Exp. Hematol.*, 17(11): 1095–1099 (1989); Bruno, E., et al., *Exp. Hematol.*, 17(10): 1038–1043 (1989); Tanikawa et al., *Exp. Hematol.*, 17(8): 883–888 (1989); Koike et al., *Blood*, 75(12): 2286–2291 (1990); Lotem, et al., *Blood,* 75(5): 1545–1551 (1989); Rennick, D., et al., *Blood,* 73(7): 1828–1835 (1989); and Clutterbuck, E. J., et al., *Blood,* 73(6): 1504–1512 (1989).

II. Thrombocytopenia

Platelets are critical elements of the blood clotting mechanism. Depletion of the circulating level of platelets, called thrombocytopenia, occurs in various clinical conditions and disorders. Thrombocytopenia is commonly defined as a platelet count below $150 \times 10^9$ per liter. The major causes of thrombocytopenia can be broadly divided into three categories on the basis of platelet life span, namely; (1) impaired production of platelets by the bone marrow, (2) platelet sequestration in the spleen (splenomegaly), or (3) increased destruction of platelets in the peripheral circulation (e.g. autoimmune thrombocytopenia or chemo- and radiation therapy). Additionally, in patients receiving large volumes of rapidly administered platelet-poor blood products, thrombocytopenia may develop due to dilution.

The clinical bleeding manifestations of thrombocytopenia depend on the severity of thrombocytopenia, its cause, and possible associated coagulation defects. In general, patients with platelet counts between 20 and $100 \times 10^9$ per liter are at risk of excessive posttraumatic bleeding, while those with platelet counts below $20 \times 10^9$ per liter may bleed spontaneously. These latter patients are candidates for platelet transfusion with attendant immune and viral risk. For any given degree of thrombocytopenia, bleeding tends to be more severe when the cause is decreased production rather than increased destruction of platelets; in the latter situation, accelerated platelet turnover results in the circulation of younger, larger and hemostatically more effective platelets. Thrombocytopenia may result from a variety of disorders briefly described below. A more detailed description may be found in Schafner, A. I., Thrombocytopenia and Disorders of Platelet Function, *Internal Medicine,* 3rd Ed., John J. Hutton et al., Eds., Little Brown and Co., Boston/Toronto/London, (1990).

(a) Thrombocytopenia Due to Impaired Platelet Production

Causes of congenital thrombocytopenia include constitutional aplastic anemia (Fanconi syndrome) and congenital amegakaryocytic thrombocytopenia, which may be associated with skeletal malformations. Acquired disorders of platelet production are caused by either hypoplasia of megakaryocytes or ineffective thrombopoiesis. Megakaryocytic hypoplasia can result from a variety of conditions, including marrow aplasia (including idiopathic forms or myelosuppression by chemotherapeutic agents or radiation therapy), myelfibrosis, leukemia, and invasion of the bone marrow by metastatic tumor or granulomas. In some situations, toxins, infectious agents, or drugs may interfere with thrombopoiesis relatively selectively; examples include transient thrombocytopenias caused by alcohol and certain viral infections and mild thrombocytopenia associated with the administration of thiazide diuretics. Finally, ineffective thrombopoiesis secondary to megaloblastic processes (folate or $B_{12}$ deficiency) can also cause thrombocytopenia, usually with coexisting anemia and leukopenia.

Current treatment of thrombocytopenias due to decreased platelet production depends on identification and reversal of the underlying cause of the bone marrow failure. Platelet transfusions are usually reserved for patients with serious bleeding complications or for coverage during surgical procedures, since isoimmunization may lead to refractoriness to further platelet transfusions. Mucosal bleeding resulting from severe thrombocytopenia may be ameliorated by the oral or intravenous administration of the antifibrinolytic agents. Thrombotic complications may develop, however, if antifibrinolytic agents are used in patients with disseminated intravascular coagulation (DIC).

(b) Thrombocytopenia Due to Splenic Sequestration

Splenomegaly due to any cause may be associated with mild to moderate thrombocytopenia. This is a largely passive process (hypersplenism) of splenic platelet sequestration, in contrast to the active destruction of platelets by the spleen in cases of immunomediated thrombocytopenia discussed below. Although the most common cause of hypersplenism is congestive splenomegaly from portal hypertension due to alcoholic cirrhosis, other forms of congestive, infiltrative, or lymphoproliferative splenomegaly are also associated with thrombocytopenia. Platelet counts generally do not fall below $50 \times 10^9$ per liter as a result of hypersplenism alone.

(c) Thrombocytopenia Due to Nonimmune-mediated Platelet Destruction

Thrombocytopenia can result from the accelerated destruction of platelets by various nonimmunologic processes. Disorders of this type include disseminated intravascular coagulation, prosthetic intravascular devices, extracorporeal circulation of the blood, and thrombotic microangiopathies such as thrombotic thrombocytic purpura. In all of these situations, circulating platelets that are exposed to either artificial surfaces or abnormal vascular intima either are consumed at these sites or are damaged and then prematurely cleared by the reticuloendothelial system. Disease states or disorders in which disseminated intravascular coagulation (DIC) may arise are set forth in greater detail in Braunwald et al: (eds), *Harrison's Principles of Internal Medicine,* 11th Ed., p.1478, McGraw Hill (1987). Intravascular prosthetic devices, including cardiac valves and intra-aortic balloons can cause a mild to moderate destructive thrombocytopenia and transient thrombocytopenia in patients undergoing cardiopulmonary bypass or hemodialysis may result from consumption or damage of platelets in the extracorporeal circuit.

(d) Drug-induced Immune Thrombocytopenia

More than 100 drugs have been implicated in immunologically mediated thrombocytopenia. However, only quinidine, quinine, gold, sulfonamides, cephalothin, and heparin have been well characterized. Drug-induced thrombocytopenia is frequently very severe and typically occurs precipitously within days while patients are taking the sensitizing medication.

(e) Immune (Autoimmune) Thrombocytopenic Purpura (ITP)

ITP in adults is a chronic disease characterized by autoimmune platelet destruction. The autoantibody is usually IgG although other immunoglobulins have also been reported. Although the autoantibody of ITP has been found to be associated with platelet membrane $GPII_bIII_a$, the platelet antigen specificity has not been identified in most cases. Extravascular destruction of sensitized platelets occurs in the reticuloendothelial system of the spleen and liver. Although over one-half of all cases of ITP are idiopathic, many patients have underlying rheumatic or autoimmune diseases (e.g. systemic lupus erythematosus) or lymphoproliferative disorders (e.g. chronic lymphocytic leukemia).

(f) HIV-Induced ITP

ITP is an increasingly common complication of HIV infection (Morris et al., *Ann. Intern. Med.,* 96: 714–717 [1982]), and can occur at any stage of the disease progression, both in patients diagnosed with the Acquired Immune Deficiency Syndrome (AIDS), those with AIDS-related complex, and those with HIV infection but without AIDS symptoms. HIV infection is a transmissible disease ultimately characterized by a profound deficiency of cellular immune function as well as the occurrence of opportunistic infection and malignancy. The primary immunologic abnormality resulting from infection by HIV is the progressive depletion and functional impairment of T lymphocytes expressing the CD4 cell surface glycoprotein (H. Lane et al., *Ann. Rev. Immunol.*, 3:477 [1985]). The loss of CD4 helper/inducer T cell function probably underlies the profound defects in cellular and humoral immunity leading to the opportunistic infections and malignancies characteristic of AIDS (H. Lane supra).

Although the mechanism of HIV-associated ITP is unknown, it is believed to be different from the mechanism of ITP not associated with HIV infection. (Walsh et al., *N. Eng. J. Med.*, 311: 635–639 [1984]; and Ratner, L., *Am. J. Med.*, 86: 194–1981 [1989]).

III. Therapy

The therapeutic approach to the treatment of patients with HIV-induced ITP is dictated by the severity and urgency of the clinical situation. The treatment is similar for HIV-associated and non-HIV-related ITP, and although a number of different therapeutic approaches have been used, the therapy remains controversial.

Platelet counts in patients diagnosed with ITP have been successfully increased by glucocorticoid (e.g. prednisolone) therapy, however in most patients the response is incomplete, or relapse occurs when the glucocorticoid dose is reduced or its administration is discontinued. Based upon studies with patients having HIV-associated ITP, some investigators have suggested that glucocorticoid therapy may result in predisposition to AIDS. Glucocorticoids are usually administered if platelet count falls below $20 \times 10^9$/liter or when spontaneous bleeding occurs.

For patients refractory to glucocorticoids, the compound 4-(2-chlorphenyl)-9-methyl-2-[3-(4-morpholinyl)-3-propanon-1-yl]6H-thieno[3,2,f][1,2,4]triazolo[4,3,a,][1,4]diazepin (WEB 2086) has been successfully used to treat a severe case of non HIV-associated ITP. A patient having platelet counts of 37,000–58,000/µl was treated with WEB 2086 and after 1–2 weeks treatment platelet counts increased to 140,000–190,000/µl. (EP 0361077A2 and Lohman, H., et al., *Lancet:*1147 [1988]).

Although the optimal treatment for acquired amegacaryocytic thrombocytopenia purpura (AATP) is uncertain, antithymocyte globulin (ATG), a horse antiserum to human thymus tissue, has been shown to produce prolonged complete remission (Trimble, M. S., et al., *Am. J. Hematol.,*37: 126–127 [1991]). A recent report however, indicates that the hematopoietic effects of ATG are attributable to thimerosal, where presumably the protein acts as a mercury carrier (Panella, T. J., and Huang, A. T., *Cancer Research:*50: 4429–4435 [1990]).

Good results have been reported with splenectomy. Splenectomy removes the major site of platelet destruction and a major source of autoantibody production in many patients. This procedure results in prolonged treatment-free remissions in a large number of patients. However, since surgical procedures are generally to be avoided in immune compromised patients, splenectomy is recommended only in severe cases of HIV-associated ITP, in patients who fail to respond to 2 to 3 weeks of glucocorticoid treatment, or do not achieve sustained response after discontinuation of glucocorticoid administration. Based upon current scientific knowledge, it is unclear whether splenectomy predisposes patients to AIDS.

In addition to prednisolone therapy and splenectomy, certain cytotoxic agents, e.g. vincristine, and azidothimidine (AZT, zidovudine) also show promise in treating HIV-induced ITP however, the results are preliminary.

It will be appreciated from the foregoing that one way to treat thrombocytopenia would be to obtain an agent capable of accelerating the differentiation and maturation of megakaryocytes or precursors thereof into the platelet-producing form. Considerable efforts have been expended on identifying such an agent, commonly referred to as "thrombopoeitin" (TPO). Thrombopoeitin activity was observed as early as 1959 (Rak et al., *Med. Exp.*1:125) and attempts to characterize and purify this agent have continued to the present day. While reports of partial purification of thrombopoeitin-active polypeptides exist (see, for example, Tayrien et al., *J. Biol. Chem.* 262:3262 [1987] and Hoffman et al.,*J. Clin. Invest.* 75:1174 [1985]), others have postulated that thrombopoeitin is not a discrete entity in its own right but rather is simply the polyfunctional manifestation of a known hormone (IL-3, Sparrow et al., *Prog. Clin. Biol. Res.,*215:123 [1986]). Regardless of its form or origin, a molecule possessing thrombopoetic activity would be of significant therapeutic value. Although no protein has been unambiguously identified as thrombopoeitin, considerable interest surrounds the recent discovery that mpl, a putative cytokine receptor, may transduce a thrombopoietic signal.

IV. Mpl is a Cytokine Receptor

It is believed that the proliferation and maturation of hematopoietic cells is tightly regulated by factors that positively or negatively modulate pluripotential stem cell proliferation and multilineage differentiation. These effects are mediated through the high-affinity binding of extracellular protein factors to specific cell surface receptors. These cell surface receptors share considerable homology and are generally classified as members of the cytokine receptor superfamily. Members of the superfamily include receptors for: IL-2 (beta and gamma chains) (Hatakeyama et al., *Science* 244:551–556 [1989]; Takeshita et al., *Science* 257:379–382 [1991]), IL-3 (Itoh et al., *Science* 247:324–328 [1990]; Gorman et al., *Proc. Natl. Acad. Sci. USA* 87:5459–5463 [1990]; Kitamura et al., *Cell* 66:1165–1174 [1991a]; Kitamura et al. *Proc. Natl. Acad. Sci. USA* 88:5082–5086 [1991b]), IL-4 (Mosley et al., *Cell* 59:335–348 [1989], IL-5 (Takaki et al. *EMBO J.* 9:4367–4374 [1990]; Tavernier et al., *Cell* 66:1175–1184 [1991]), IL-6 (Yamasaki et al., *Science* 241:825–828 [1988]; Hibi et al. *Cell* 63:1149–1157 [1990]), IL-7 (Goodwin et al. *Cell* 60:941–951 [1990]), IL-9 (Renault et al. *Proc. Natl. Acad. Sci. USA* 89:5690–5694 [1992]), granulocyte-macrophage colony-stimulating factor (GM-CSF) (Gearing et al., *EMBO J.* 8:3667–3676 [1991]; Hayashida et al. *Proc. Natl. Acad. Sci. USA* 244:9655–9659 [1990]), granulocyte colony-stimulating factor (G-CSF) (Fukunaga et al., *Cell* 61:341–350 [1990a]; Fukunaga et al. *Proc. Natl. Acad. Sci. USA* 87:8702–8706 [1990b]; Larsen et al. *J. Exp. Med.* 172:1559–1570 [1990]), erythropoietin (EPO) (D'Andrea et al., *Cell* 57:277–285 [1989]; Jones et al., *Blood* 76:31–35 [1990]), Leukemia inhibitory factor (LIF) (Gearing et al., *EMBO J.* 10:2839–2848 [1991]), oncostatin M (OSM) (Rose et al., *Proc. Natl. Acad. Sci. USA* 88:8641–8645 [1991]) and also receptors for prolactin (Boutin et al., *Proc. Natl. Acad. Sci. USA* 88:7744–7748 [1988]; Edery et al., *Proc. Natl. Acad. Sci. USA* 86:2112–2116 [1989]), growth hormone (GH) (Leung et al., *Nature* 330:537–543 [1987]) and ciliary neurotrophicfactor (CNTF) (Davis et al., *Science* 253:59–63 [1991].

Members of the cytokine receptor superfamily may be grouped into three functional categories (for review see Nicola et al., *Cell* 67:1–4 [1991]). The first class comprises single chain receptors, such as erythropoietin receptor (EPO-R) or granulocyte colony stimulating factor receptor (G-CSF-R) bind ligand with high affinity via the extracellular domain and also generate an intracellular signal. A second class of receptors, so call α-subunits, includes interleukin-6 receptor (IL6-R), granulocyte-macrophage colony stimulating factor receptor (GM-CSF-R), interleukin-3 receptor (IL3-Rα) and other members of the cytpkine receptor superfamily. These α-subunits bind ligand with low affinity but cannot transduce an intracellular signal. A high affinity receptor capable of signaling is generated by a heterodimer between an α-subunit and a member of a third class of cytokine receptors, termed β-subunits, e.g. $β_c$, the common β-subunit for the three α-subunits IL3-Rα and GM-CSF-R.

Evidence that mpl is a member of the cytokine receptor superfamily comes from sequence homology (Gearing, D. P., *EMBO J.* 8:3667–3676 [1988]; Bazan, J. F., *Proc. Natl. Acad. Sci. USA* 87:6834–6938 [1990]; Davis S., et al., *Science* 253:59–63 [1991] and Vigon et al., *Proc. Natl. Acad. Sci. USA* 89:5640–5644 [1992]) and its ability to transduce proliferative signals.

Deduced protein sequence from molecular cloning of murine c-mpl reveals this protein is homologous to other cytokine receptors. The extracellular domain contains 465 amino acid residues and is composed of two subdomains each with four highly conserved cysteines and a WGXWS motif in the N-terminal subdomain and WSXWS motif in the C-terminal subdomain. The ligand-binding extracellular domains are predicted to have similar double β-barrel fold structural geometries. This duplicated extracellular domain is highly homologous to the signal transducing chain common to IL-3, IL-5 and GM-CSF receptors as well as the low-affinity binding domain of LIF (Vigon I., et al., *Oncogene* 8:2607–2615 [1993]). Thus mpl may belong to the low affinity ligand binding class of cytokine receptors.

The extracellular domain is followed by a 22 residue transmembrane domain and a 121 residue cytoplasmic domain rich in serine and proline. The cytoplasmic domain contains no consensus protein kinase, phosphotase or any other known motif associated with signal transduction.

A comparison of murine mpl and mature human mpl P, reveals these two proteins show 81% sequence identity. More specifically, the N-terminus and C-terminus extracellular subdomains share 75% and 80% identity respectively. The most conserved mpl region is the cytoplasmic domain showing 91% amino acid identity, with a sequence of 37 residues near the transmembrane domain being identical in both species. Accordingly, mpl is reported to be one of the most conserved members of the cytokine receptor superfamily (Vigon supra).

Evidence that mpl is a functional receptor capable of transducing a proliferative signal comes from construction of chimeric receptors containing an extracellular domain from a cytokine receptor having high affinity for a known cytokine with the mpl cytoplasmic domain. Since no known ligand for mpl has been reported, it was necessary to construct the chimeric high affinity ligand binding extracellular domain from a class one cytokine receptor such as IL-4R or G-CSFR. Vigon et al. supra fused the extracellular domain of G-CSFR with both the transmembrane and cytoplasmic domain of c-mpl. An IL-3 dependent cell line, BAF/B03 was transfected with the G-CSFR/mpl chimera along with a full length G-CSFR control. Cells transfected with the chimera grew equally well in the presence of cytokine IL-3 or G-CSF. Similarly, cells transfected with G-CSFR also grew well in either IL-3 or G-CSF. All cells died in the absence of growth factors. A similar experiment was conducted by Skoda, R. C. et al. *EMBO J.* 12(7):2645–2653 (1993) in which both the extracellular and transmrembrane domains of human IL4 receptor (hIL4-R) were fused to the murine mpl cytoplasmic domain, and transfected into a murine IL3 dependent Ba/F3 cell line. Ba/F3 cells transfected with wildtype hIL4-R proliferated normally in either the presence of the species specific IL-4 or IL-3. BaF3 cells transfected with hIL4R/mpl proliferated normally in the presence of hIL4 (in the presence or absence of IL3) demonstrating that in Ba/F3 cells the mpl cytoplasmic domain contains all the elements necessary to transduce a proliferative signal.

These chimeric experiments demonstrate the proliferation signaling capability of the mpl extracellular domain but are silent regarding whether the mpl extracellular domain can bind a ligand. These results are consistent with at least two possibilities, namely, mpl is a single chain (class one) receptor like EpoR or G-CSFR or it is a signal transducing β-subunit (class three) requiring an α-subunit like IL-3 (Skoda et al. supra).

V. Mpl Ligand Stimulates Megakaryocytopoiesis

As described above, it has been suggested that serum contains a unique factor, sometimes referred to as thrombopoietin, that acts synergistically with various other cytokines to promote growth and maturation of megakaryocytes. No such natural factor has ever been isolated from serum or any other source even though considerable effort has been expended by numerous groups. Even though it is not know whether mpl is capable of directly binding a megakaryocyte stimulating factor, recent experiments demonstrate that mpl is involved in proliferative signal transduction from a factor or factors found in the serum of patients with aplastic bone marrow (Methia, N. et al., *Blood* 82(5):1395–1401 [1993]).

Evidence that a unique serum colony-forming factor distinct from IL-1α, IL-3, IL-4, IL-6, IL-11, SCF, EPO, G-CSF, and GM-CSF transduces a proliferative signal through mpl comes from examination of the distribution of c-mpl expression in primitive and committed hemotopoietic cell lines and from mpl antisense studies in one of these cell lines.

Using reverse transcriptase (RT)-PCR in immuno-purified, human hematopoietic cells Methia et al. supra demonstrated that strong mpl mRNA messages were only found in CD34+ purified cells, megakaryocytes and platelets. CD34+ cells purified from Bone Marrow (BM) represents about 1% of all BM cells and are enriched in primitive and committed progenitors of all lineages (e.g. erythroid, granulomacrophage, and megakaryocytic).

Mpl antisense oligodeoxy nucleotides were shown to suppress megakaryocytic colony formation from the pluripotent CD34+ cells cultured in serum from patients with aplastic marrow (a rich source of megakaryocytes stimulating activity [Meg-CSA]). These same antisense oligodeoxy-nucleotides had no effect on erythroid or granulomacrophage colony formation.

Whether mpl directly binds a ligand and whether the serum factor shown to cause megakaryocytopoiesis acts through mpl is still unknown. It has been suggested, however, that if mpl does directly bind a ligand, its amino acid sequence is likely to be highly conserved and have species cross reactivity owing to the considerable sequence identity between human and murine mpl extracellular domain (Vigon et al., supra[1993]).

In view of the foregoing it will be appreciated there is a current and continuing need in the art to isolate and identify molecules capable of stimulating differentiation and maturation of megakaryocytes for therapeutic use in the treatment of thrombocytopenia. It is believed such a molecule is a mpl ligand and thus there exists a further need to isolate such ligand(s) to evaluate their role(s) in cell growth and differentiation.

Accordingly, it is an object of this invention to obtain a novel pharmaceutically pure molecule capable of stimulating differentiation and maturation of megakaryocytes into the mature platelet-producing form.

It is another object to provide the novel molecule in a form for therapeutic use in the treatment of thrombocytopenia.

It is a further object of the present invention to isolate, purify and specifically identify novel protein ligands capable of binding in vivo a cytokine superfamily receptor known as mpl and to transduce a proliferative signal.

It is still another object to provide novel nucleic acid molecules encoding such protein ligands and to use this nucleic acid molecule to produce mpl binding ligands in recombinant cell culture for diagnostic and therapeutic use.

It is yet another object to provide derivatives and modified forms of the protein ligands including amino acid sequence variants, novel glycoprotein forms and other covalent derivatives thereof.

It is an additional object to provide fusion polypeptide forms combining a novel mpl ligand and a heterologous protein and covalent derivatives thereof.

It is yet an additional object to prepare immunogens for raising antibodies against novel mpl ligands or fusion forms thereof, as well as to obtain antibodies capable of binding such ligands.

These and other objects of the invention will be apparent to the ordinary artisan upon consideration of the specification as a whole.

SUMMARY OF THE INVENTION

The objects of the invention are achieved by providing an isolated mammalian megakaryocytopoietic maturation promoting protein capable of stimulating maturation and/or differentiation of megakaryocytes into the mature platelet-producing form. This substantially homogeneous protein denominated the "mpl ligand" is purified from a natural source by the procedures described herein and has the following characteristics:

(1) The partially purified ligand isolated from aplastic porcine plasma elutes from a gel filtration run in either PBS, PBS containing 0.1% SDS or PBS containing 4M $MgCl_2$ with Mr of 60,000–70,000;

(2) The ligand's activity is destroyed by pronase;

(3) The ligand is stable to low pH (2.5), SDS to 0.1%, and 2M urea;

(4) The ligand is a glycoprotein, based on its binding to a variety of lectin columns;

(5) The highly purified ligand elutes from non-reduced SDS-PAGE with a Mr of 25,000–35,000. Smaller amounts of activity also elute with Mr of ~18,000 and 60,000;

(6) The highly purified ligand resolves on reduced SDS-PAGE as a doublet with Mr of 28,000 and 31,000;

(7) The amino-terminal sequence of the 18,000, 28,000 and 31,000 bands is the same—SPAPPACDPRLLNKLLRDDH SEQ ID NO.: 1); and (8) The ligand binds and elutes from the following affinity columns Blue-Sepharose,
CM Blue-Sepharose,
MONO-Q,
MONO-S,
Lentil lectin-Sepharose,
WGA-Sepharose,
CON A-Sepharose,
Ether 650 m Toyopearl,
Butyl 650 m Toyopearl,
Phenyl 650 m Toyopearl, and
Phenyl-Sepharose.

The "mpl ligand" polypeptide of this invention preferably has at least 80% sequence identity with the amino acid sequence of the highly purified mpl ligand isolated from aplastic porcine plasma described herein. Most preferably the mpl ligand of this invention is mature human mpl ligand or a protein having 80% sequence identity with mature human mpl ligand. Optionally the mpl ligand polypeptide or fragment thereof may be fused to a heterologous polypeptide. A preferred heterologous polypeptide is a cytokine.

Another aspect of this invention provides a composition comprising an isolated mpl ligand capable of stimulating the incorporation of labeled nucleotides ($^3$H-thymidine) into the DNA of IL-3 dependent Ba/F3 cells transfected with human mpl P and isolated from its source environment sufficiently free of contaminating source proteins to yield an unambiguous N-terminus amino acid sequence of at least 20 residues. In one embodiment, the N-terminus amino acid sequence of this ligand is SPAPPACDPRLLNKLLRDDH (SEQ ID NO.: 1). Optionally, the ligand of this invention has a portion of its amino acid sequence at or near its N-terminus that has at least 80% sequence identity with the sequence; SPAPPACDPRLLNKLLRDDH (SEQ ID NO.:1).

In still another aspect, a method is provided for purifying mpl ligand molecules comprising contacting a source plasma containing the mpl ligand molecules to be purified with an immobilized receptor polypeptide, specifically mpl or a mpl fusion polypeptide immobilized on a support, under conditions whereby the mpl ligand molecules to be purified are selectively adsorbed onto the immobilized receptor polypeptide, washing the immobilized support to remove non-adsorbed material, and eluting the molecules to be purified from the immobilized receptor polypeptide to which they are adsorbed with an elution buffer. Preferably the source plasma containing the mpl ligand is aplastic porcine plasma and the immobilized receptor is a mpl-IgG fusion. Also preferably the immobilized support is washed with PBS/PBS in 2M NaCl and the elution buffer is 0.1M glycine-HCl, pH 2.25.

In another embodiment, this invention provides an isolated antibody capable of binding to the mpl ligand. The isolated antibody capable of binding to the mpl ligand may optionally be fused to a second polypeptide and the antibody or fusion thereof may be used to isolate and purify mpl ligand from a source as described above for immobilized mpl polypeptide. In a further aspect of this embodiment, the invention provides a method for detecting the mpl ligand in vitro or in vivo comprising contacting the antibody with a sample, especially a serum sample, suspected of containing the ligand and detecting if binding has occurred.

In still further embodiments, the invention provides an isolated nucleic acid molecule, encoding the mpl ligand or fragments thereof, which nucleic acid molecule may be labeled or with a detectable moiety, and a nucleic acid molecule having a sequence that is complementary to, or hybridizes under stringent or moderately stringent conditions with, a nucleic acid molecule having a sequence encoding a mpl ligand. In a further aspect of this embodiment, the nucleic acid molecule is DNA encoding the mpl ligand and further comprises a replicable vector in which the DNA is operably linked to control sequences recognized by a host transformed with the vector. This aspect further includes host cells transformed with the vector and a method of using the DNA to effect production of mpl ligand, comprising expressing the DNA encoding the mpl ligand in a culture of the transformed host cells and recovering the mpl ligand from the host cells or the host cell culture. The mpl ligand prepared in this manner is preferably human mpl ligand.

The invention further includes a method for treating a mammal having thrombocytopenia comprising administering a therapeutically effective amount of a mpl Ligand to the mammal. Optionally the mpl Ligand is administered in combination with a cytokine, especially a colony stimulating factor or interleukin. Preferred colony stimulating factors or interleukins include; G-CSF, CSF-1, GM-CSF, M-CSF, erythropoietin, IL-1, IL-3, IL-4, IL-5, IL-6, IL-7, IL-8, or IL-11.

DETAILED DESCRIPTION OF THE INVENTION

I. Definitions

Figure 1:
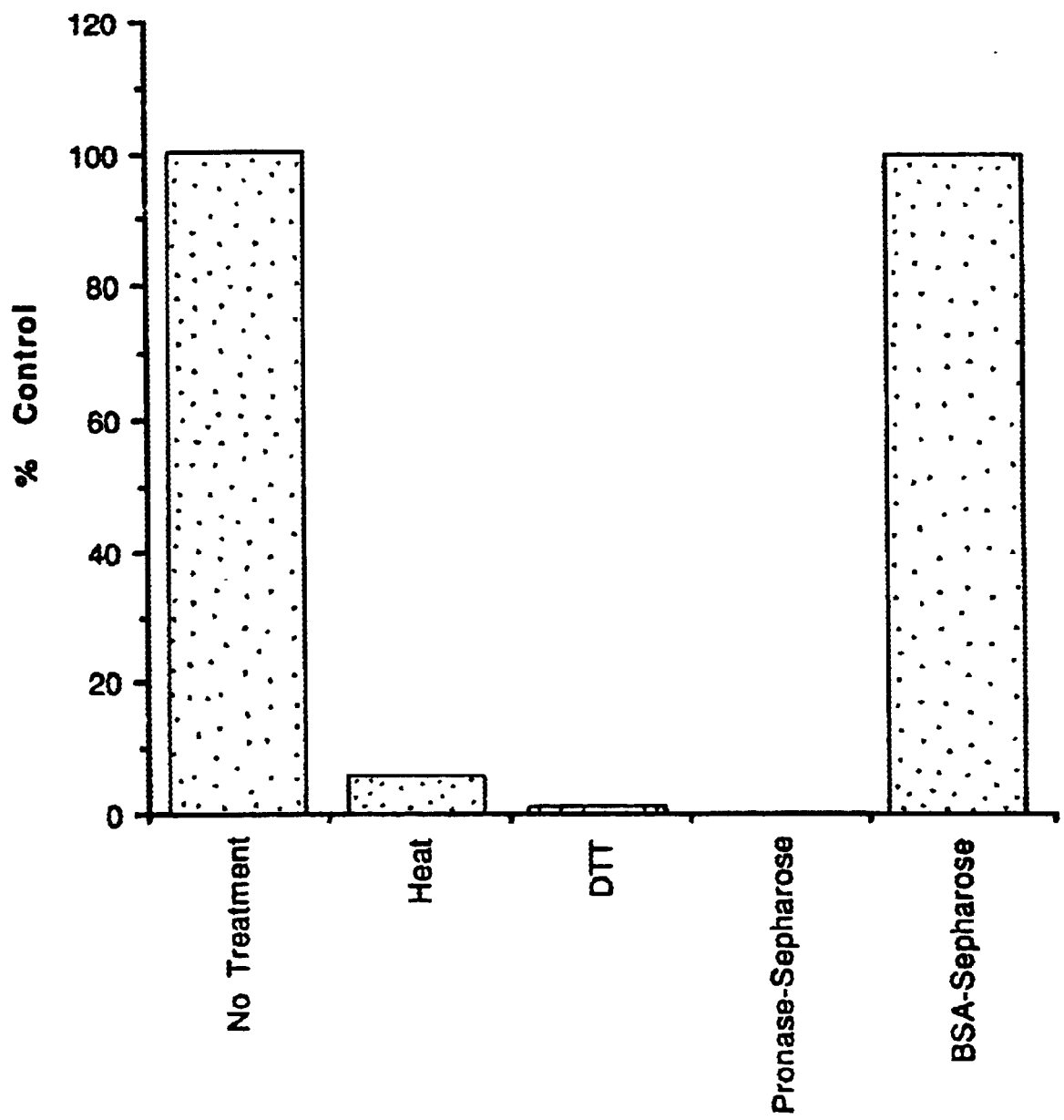
FIG. 1. Effect of pronase, DTT and heat on the ability of APP to stimulate Ba/F3-mpl cell proliferation. For prohase digestion of APP, pronase (Boehringer Mannheim) or bovine serum albumin was coupled to affi-gel10 (Biorad) and incubated individually with APP for 18 hrs. at 37 C. Subsequently, the resins were removed by centrifugation and supernatants asayed. APP was also heated to 80 C. for 4 min. or made 100 uM DTT followed by dialysis against PBS.

In general, the following words or phrases have the indicated definition when used in the description, examples, and claims.

"Cytokine" is a generic term for proteins released by one cell population which act on another cell as intercellular mediators. Examples of such cytokines are lymphokines, monokines, and traditional polypeptide hormones. Included among the cytokines are growth hormone, insulin-like growth factors, human growth hormone, N-methionyl human growth hormone, bovine growth hormone, parathyroid hormone, thyroxine, insulin, proinsulin, relaxin, prorelaxin, glycoprotein hormones such as follicle stimulating hormone (FSH), thyroid stimulating hormone (TSH), and leutinizing hormone (LH), hemopoietic growth factor, hepatic growth factor, fibroblast growth factor, prolactin, placental lactogen, tumor necrosis factor-alpha and -beta, mullerian-inhibiting substance, mouse gonadotropin-associated peptide, inhibin, activin, vascular endothelial growth factor, integrin, thrombopoietin, nerve growth factors such as NGF-β, platelet-growth factor, transforming growth factors (TGFs) such as TGF-alpha and TGF-beta, insulin-like growth factor-I and -II, erythropoietin, osteoinductive factors, interferons such as interferon-alpha, -beta, and -gamma, colony stimulating factors (CSFs) such as macrophage-CSF (M-CSF), granulocyte-macrophage-CSF (GM-CSF), and granulocyte-CSF (G-CSF), interleukins (ILs) such as IL-1, IL-2, IL-3, IL-4, IL-5, IL-6, IL-7, IL-8 and other polypeptide factors. As used herein the foregoing terms are meant to include proteins from natural sources or from recombinant cell culture. Similarly, the terms are intended to include biologically active equivalents; e.g. differing in amino acid sequence by one or more amino acids or in type or extent of glycosylation.

A "mpl ligand" is any polypeptide that possesses the property of binding to mpl, a member of the cytokine receptor superfamily, and having a biological property of the mpl ligand defined below. The preferred biological property is the ability to stimulate the incorporation of labeled nucleotides (e.g. $^3$H-thymidine) into the DNA of IL-3 dependent Ba/F3 cells transfected with human mpl P. This definition encompasses the poylpeptide isolated from aplastic porcine plasma described herein or from another source and includes functional derivatives, fragments, alleles, isoforms and analogus thereof.

"Isolated mpl ligand", "highly purified mpl ligand" and "substantially homogenous mpl ligand" are used interchangeably and mean a mpl ligand that has been purified from a mpl ligand source and is sufficiently free of other source proteins (1) to obtain at least 15 and preferably 20 amino acid residues of the N-terminal or of an internal amino acid sequence by using a spinning cup sequenator or the best commercially available amino acid sequenator marketed or as modified by published methods as of the filing date of this application, or (2) to homogeneity by SDS-PAGE under non-reducing or reducing conditions using Coomassie blue or, preferably, silver stain. Homogeneity here means less then 5% contaminated with other source proteins.

"Biological property" when used in conjunction with either the "mpl ligand" or "Isolated mpl ligand" means an in vivo effector or antigenic function or activity that is directly or indirectly caused or performed by a mpl ligand (whether in its native or denatured conformation) or a fragment thereof. Effector functions include mpl binding and any carrier binding activity, agonism or antagonism of mpl, especially transduction of a proliferative signal including replication, DNA regulatory function, modulation of the biological activity of other cytokines, receptor (especially cytokine) activation, deactivation, up- or down regulation, cell growth or differentiation and the like. An antigenic function means possession of an epitope or antigenic site that is capable of cross-reacting with antibodies raised against the mpl ligand.

"Biologically active" when used in conjunction with either the "mpl ligand" or "Isolated mpl ligand" means a mpl ligand or polypeptide that shares an effector and/or antigenic function of the mpl ligand isolated from aplastic porcine plasma described herein. A principal known effector function of the mpl ligand or polypeptide herein is binding to mpl and stimulating the incorporation of labeled nucleotides ($^3$H-thymidine) into the DNA of IL-3 dependent Ba/F3 cells transfected with human mpl P. The principal antigenic function of a mpl ligand polypeptide is that it binds with an affinity of at least about $10^6$ l/mole to an antibody raised against the mpl ligand isolated from aplastic porcine plasma. Ordinarily, the polypeptide binds with an affinity of at least about $10^7$ l/mole. Most preferably, the antigenically active mpl ligand polypeptide is a polypeptide that binds to an antibody raised against the mpl ligand having one of the above described effector functions. The antibodies used to define "biologically activity" are rabbit poly clonal antibodies raised by formulating the mpl ligand isolated from aplastic porcine plasma in Freund's complete adjuvant, subcutaneously injecting the formulation, and boosting the immune response by intraperitoneal injection of the formulation until the titer of mpl ligand antibody plateaus.

"Percent amino acid sequence Identity" with respect to the mpl ligand sequence is defined herein as the percentage of amino acid residues in the candidate sequence that are identical with the residues in the mpl ligand sequence isolated from aplastic porcine plasma after aligning the sequences and introducing gaps, if necessary, to achieve the maximum percent sequence identity, and not considering any conservative substitutions as part of the sequence identity. None of N-terminal, C-terminal, or internal extensions, deletions, or insertions into the mpl ligand sequence isolated from aplastic porcine plasma shall be construed as affecting sequence identity or homology. Thus exemplary biologically active mpl ligand polypeptides considered to have identical sequences include; prepro-mpl ligand, pro-mpl ligand, and mature mpl ligand.

"Mpl ligand microsequencing" may be accomplished by any appropriate standard procedure provided the procedure is sensitive enough. In one such method, highly purified polypeptide obtained from SDS gels or from a final HPLC step are sequenced directly by automated Edman (phenyl isothiocyanate) degradation using a model 470A Applied Biosystems gas phase sequencer equipped with a 120A phenylthiohydantion (PTH) amino acid analyzer. Additionally, mpl ligand fragments prepared by chemical (e.g. CNBr, hydroxylamine, 2-nitro-5-thiocyanobenzoate) or enzymatic (e.g. trypsin, clostripain, staphylococcal protease) digestion followed by fragment purification (e.g. HPLC) may be similarly sequenced. PTH amino acids are analyzed using the ChromPerfect data system (Justice Innovations, Palo Alto, Calif.). Sequence interpretation is performed on a VAX 11/785 Digital Equipment Co. computer as described by Henzel et al.,*J. Chromatography* 404:41–52 (1987). Optionally, aliquots of HPLC fractions may be electrophoresed on 5–20% SDS-PAG, electrotransfered to a PVDF membrane ProBlott, AIB, Foster City, Calif.) and stained with Coomassie Brilliant Blue (Matsudiara, P.,*J. Biol. Chem.* 262:10035–10038 (1987). A specific protein identified by the stain is excised from the Blot and N-terminal sequencing is carried out with the gas phase sequenator described above. For internal protein sequences, HPLC fractions are dried under vacuum (SpeedVac), resuspended in appropriate buffers, and digested with cyanogen bromide, the Lys-specific enzyme Lys-C (Wako Chemicals, Richmond, Va.), or Asp-N (Boehringer Mannheim, Indianapolis, Ind.). After digestion, the resultant peptides are sequenced as a mixture or after HPLC resolution on a C4 column developed with a propanol gradient in 0.1% TFA prior to gas phase sequencing.

"Mpl ligand variants" or "Mpl ligand sequence variants" as defined herein means a biologically active mpl ligand as defined above having less than 100% sequence identity with the mpl ligand isolated from aplastic porcine plasma described herein. Ordinarily, a biologically active mpl ligand variant will have an amino acid sequence having at least 70% amino acid sequence identity with the mpl ligand isolated from aplastic porcine plasma, preferably at least 75%, more preferably at least 80%, still more preferably at least 85%, even more preferably at least 90%, and most preferably at least 95%.

"Mpl ligand fragments" as used herein have a consecutive sequence of at least 10, 15, 20, 25, 30, or 40 amino acid residues that are identical to the sequences of the mpl ligand isolated from aplastic porcine plasma described herein. An example of a mpl ligand fragment is the N-terminal domain ("NTD") having the sequence SPAPPACDPRLLNKLLRD-DHVLHGR SEQ ID NO.: 2). Other examples of mpl ligand fragments include those produced as a result of chemical or enzymatic digestion of the purified ligand as described above under "Mpl ligand microsequencing".

"Thrombocytopenia" is defined as a platelet count below $150\times10^9$ per liter of blood.

"Thrombopoeitic activity" is defined as biological activity that consists of accelerating the differentiation and/or maturation of megakaryocytes or megakaryocyte precursors into the platelet producing form of these cells. This activity may be measured in various assays including an in-vivo mouse platelet rebound synthesis assay, induction of platelet cell surface antigen assay as measured by an anti-platelet immunoassay (anti-GPII$_b$III$_a$) for a human leukemia megakaryoblastic cell line (CMK), and induction of polyploidization in a megakaryoblastic cell line(DAMI).

"Thrombopoeitin" (TPO) is defined as a compound having Thrombopoeitic activity or being capable of increasing serum platelet counts in a mammal. TPO is preferably capable of increasing endogenous platelet counts by at least 10%, more preferably by 50%, and most preferably capable of elevating platelet counts in a human to greater that $150\times10^9$ per liter of blood.

"Isolated mpl ligand nucleic ac id" is RNA or DNA containing greater than 16, preferably 20 or more, sequential nucleotide bases that encode biologically active mpl ligand or a fragment thereof, is complementary to the RNA or DNA, or hybridizes to the RNA or DNA and remains stably bound under stringent conditions. This RNA or DNA is free from at least one contaminating source nucleic acid with which it is normally associated in the natural source and preferably substantially free of any other mammalian RNA or DNA. The phrase "free from at least one contaminating source nucleic acid with which it is normally associated" includes the case where the nucleic acid is present in the source or natural cell but is in a different chromosomal location or is otherwise flanked by neucleic acid sequences not normally found in the source cell. An example of isolated mpl ligand nucleic acid is RNA or DNA that encodes a biologically active mpl ligand sharing at least 75% sequence identity, more preferably at least 80%, still more preferably at least 85%, even more preferably 90%, and most preferably 95% sequence identity with the porcine mpl ligand.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribbsome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

"Exogenous" when referring to an element means a nucleic acid sequence that is foreign to the cell, or homologous to the cell but in a position within the host cell nucleic acid in which the element is ordinarily not found.

"Cell," "cell line," and "cell culture" are used interchangeably herein and such designations include all progeny of a cell or cell line. Thus, for example terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Plasmids" are autonomously replicating circular DNA molecules possessing independent origins of replication and are designated herein by a lower case "p" preceded and/or followed by capital letters and/or numbers. The starting plasmids herein are either commercially available, publicly available on an unrestricted basis, or can be constructed from such available plasmids in accord with published procedures. In addition, other equivalent plasmids are known in the art and will be apparent to the ordinary artisan.

"Restriction enzyme digestion" when referring to DNA means catalytic cleavage of internal phosphodiester bonds of DNA with an enzyme that acts only at certain locations or sites in the DNA sequence. Such enzymes are called "restriction endonucleases". Each restriction endonuclease recognizes a specific DNA sequence called a "restriction site" that exhibits twofold symmetry. The various restriction enzymes used herein are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 μg of plasmid or DNA fragment is used with about 1–2 units of enzyme in about 20 μl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein or polypeptide is removed by extraction with phenol and chloroform, and the digested nucleic acid is recovered from the aqueous fraction by precipitation with ethanol. Digestion with a restriction enzyme may be followed with bacterial alkaline phosphatase hydrolysis of the terminal 5' phosphates to prevent the two restriction-cleaved ends of a DNA fragment from "circularizing" or forming a closed loop that would impede insertion of another DNA fragment at the restriction site. Unless otherwise stated, digestion of plasmids is not followed by 5' terminal dephosphorylation. Procedures and reagents for dephosphorylation are conventional as described in sections 1.56–1.61 of Sambrook et al., *Molecular Cloning: A Laboratory Manual* [New York: Cold Spring Harbor Laboratory Press, 1989].

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al., *Nucleic Acids Res.*, 9:6103–6114 (1981), and Goeddel et al., *Nucleic Acids Res.* 8:4057 (1980).

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as 32-P, or by biotinylation, or with an enzyme. The RNA to be analyzed is usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation. The DNA fragments that are to be ligated together are put in solution in about equimolar amounts. The solution will also contain ATP, ligase buffer, and a ligase such as T4 DNA ligase at about 10 units per 0.5 µg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

"Preparation" of DNA from cells means isolating the plasmid DNA from a culture of the host cells. Commonly used methods for DNA preparation are the large- and small-scale plasmid preparations described in sections 1.25–1.33 of Sambrook et al., supra. After preparation of the DNA, it can be purified by methods well known in the art such as that described in section 1.40 of Sambrook et al., supra.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published May 4, 1988, or via deoxynucleoside H-phosphonate intermediates as described by Froehler et al., *Nucl. Acids Res.,* 14: 5399–5407 [1986]. Further methods include the polymerase chain reaction defined below and other autoprimer methods and oligonucleotide syntheses on solid supports. All of these methods are described in Engels et al., *Agnew. Chem. Int. Ed. Engl.,* 28: 716–734 [1989]). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides are then purified on polyacrylamide gels.

"Polymerase chain reaction" or "NPCR" refers to a procedure or technique in which minute amounts of a specific piece of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51: 263 (1987); Erlich, ed., *PCR Technology,* (Stockton Press, NY, 1989). As used herein, PCR is considered to be one, but not the only, example of a nucleic acid polymerase reaction method for amplifying a nucleic acid test sample comprising the use of a known nucleic acid as a primer and a nucleic acid polymerase to amplify or generate a specific piece of nucleic acid.

"Stringent conditions" are those that (1) employ low ionic strength and high temperature for washing, for example, 0.015 M NaCl/0.0015 M sodium citrate/0.1%. NaDodSO$_4$ at 50° C., or (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

II. Preferred Embodiments of the Invention

Preferred polypeptides of this invention are substantially homogeneous polypeptide(s), refered to as mpl ligand(s), that possesses the property of binding to mpl, a member of the receptor cytokine superfamily, and having the biological property of stimulating the incorporation of labled nucleotides ($^3$H-thymidine) into the DNA of IL-3 dependant Ba/F3 cells transfected with human mpl P. More preferred mpl ligand(s) are isolated mammalian protein(s) having thrombopoeitic activity, namely, being capable of stimulating maturation and/or differentiation of immature megakaryocytes into the mature platelet-producing form. Most preferred polypeptides of this invention are human mpl ligand(s) having thrombopoeitic activity. Optionally these human mpl ligand(s) lack glycosylation.

Optional preferred polypeptides of this invention are biologically active mpl ligand variant(s) that have an amino acid sequence having at least 70% amino acid sequence identity with the mpl ligand isolated from aplastic porcine plasma, preferably at least 75%, more preferably at least 80%, still more preferably at least 85%, even more preferably at least 90%, and most preferably at least 95%. The mpl ligand isolated from aplastic porcine plasma has the following characteristics:

(1) The partially purified ligand isolated from aplastic porcine plasma elutes from a gel filtration run in either PBS, PBS containing 0.1% SDS or PBS containing 4M MgCl$_2$ with Mr of 60,000–70,000;

(2) The ligand's activity is destroyed by pronase;

(3) The ligand is stable to low pH (2.5), SDS to 0.1%, and 2M urea;

(4) The ligand is a glycoprotein, based on its binding to a variety of lectin columns;

(5) The highly purified-ligand elutes from non-reduced SDS-PAGE with a Mr of 25,000–35,000. Smaller amounts of activity also elute with Mr of ~18,000 and 60,000;

(6) The highly purified ligand resolves on reduced SDS-PAGE as a doublet with Mr of 28,000 and 31,000;

(7) The amino-terminal sequence of the 18,000, 28,000 and 31,000 bands is the same— SPAPPACDPRLLNKLLRDDHVLHGR (SEQ ID NO.: 2); and (8) The ligand binds and elutes from the following affinity columns
Blue-Sepharose,
CM Blue-Sepharose,
MONO-Q,
MONO-S,
Lentil lectin-Sepharose,
WGA-Sepharose,
CON A-Sepharose,
Ether 650 m Toyopearl,
Butyl 650 m Toyopearl,
Phenyl 650 m Toyopearl, and
Phenyl-Sepharose.

Other preferred naturally occuring biologically active mpl ligand polypeptides of this invention include; prepro-mpl ligand, pro-mpl ligand, mature mpl ligand and glycosylation variants thereof.

Still other preferred polypeptides of this invention include Mpl ligand sequence variants. Ordinarily, preferred Mpl ligand sequence variants are biologically active mpl ligand variants that have an amino acid sequence having at least 70% amino acid sequence identity with the mpl ligand isolated from aplastic porcine plasma, preferably at least 75%, more preferably at least 80%, still more preferably at least 85%, even more preferably at least 90%, and most preferably at least 95%. An exemplary preferred variant is a fusion between mpl ligand or fragment (defined below) thereof and another cytokine or fragment thereof.

Other preferred polypeptides of this invention include Mpl ligand fragments having a consecutive sequence of at least 10, 15, 20, 25, 30, or 40 amino acid residues that are identical to the sequences of the mpl ligand isolated from aplastic porcine plasma described herein. A preferred mpl ligand fragment is the N-terminal domain ("NTD") having the sequence SPAPPACDPRLLNKLLRDDHVLHGR (SEQ ID NO: 2). Other preferred mpl ligand fragments include those produced as a result of chemical or enzymatic digestion of the purified ligand.

Another preferred aspect of the invention, is a method for purifying mpl ligand molecules comprises contacting a mpl ligand source containing the mpl ligand molecules to be purified with an immobilized receptor polypeptide, specifically mpl or a mpl fusion polypeptide, under conditions whereby the mpl ligand molecules to be purified are selectively adsorbed onto the immobilized receptor polypeptide, washing the immobilized support to remove non-adsorbed material, and eluting the molecules to be purified from the immobilized receptor polypeptide to which they are adsorbed with an elution buffer. Preferably the source containing the mpl ligand is plasma, more preferably aplastic porcine plasma and the immobilized receptor is preferably a mpl-IgG fusion. Also preferably the immobilized support is washed with PBS/PBS in 2M NaCl and the elution buffer is 0.1M glycine-HCl, pH 2.25.

In another preferred embodiment, this invention provides an isolated antibody capable of binding to the mpl ligand. Preferred mpl ligand isolated antibody is one that binds to mpl ligand with an affinity of at least about $10^6$ l/mole. More preferably the antibody binds with an affinity of at least about $10^7$ l/mole. Most preferably, the antibody is raised against the mpl ligand having one of the above described effector functions. The isolated antibody capable of binding to the mpl ligand may optionally be fused to a second polypeptide and the antibody or fusion thereof may be used to isolate and purify mpl ligand from a source as described above for immobilized mpl polypeptide. In a further preferred aspect of this embodiment, the invention provides a method for detecting the mpl ligand in vitro or in vivo comprising contacting the antibody with a sample, especially a serum sample, suspected of containing the ligand and detecting if binding has occurred.

In still further preferred embodiments, the invention provides an isolated nucleic acid molecule, encoding the mpl ligand or fragments thereof, which nucleic acid molecule may be labeled or unlabled with a detectable moiety, and a nucleic acid molecule having a sequence that is complementary to, or hybridizes under stringent or moderately stringent conditions with, a nucleic acid molecule having a sequence encoding a mpl ligand. Moderately stringent conditions are conditions such as overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextrane sulfate, and 20 µl/ml denatured sheared salmon sperm DNA, followed by washing the filters in 1×SSC at about 50° C. A preferred mpl ligand nucleic acid is RNA or DNA that encodes a biologically active mpl ligand sharing at least 75% sequence identity, more preferably at least 80%, still more preferably at least 85%, even more preferably 90%, and most preferably 95% sequence identity with the porcine mpl ligand.

In a further preferred aspect of this embodiment, the nucleic acid molecule is DNA encoding the mpl ligand and further comprises a replicable vector in which the DNA is operably linked to control sequences recognized by a host transformed with the vector. This aspect further includes host cells transformed with the vector and a method of using the DNA to effect production of mpl ligand, comprising expressing the DNA encoding the mpl ligand in a culture of the transformed host cells and recovering the mpl ligand from the host cell culture. The mpl ligand prepared in this manner is preferably human mpl ligand.

The invention further includes a preferred method for treating a mammal having thrombocytopenia comprising administering a therapeutically effective amount of a mpl Ligand to the mammal. Preferably the mpl Ligand is administered in combination with a cytokine, especially a colony stimulating factor or interleukin. Preferred colony stimulating factors or interleukins include; G-CSF, CSF-1, GM-CSF, M-CSF, erythropoietin, IL-1, IL-3, IL-4, IL-5, IL-6, IL-7, or IL-8.

III. Methods of Making

1. Purification and Identification of mpl Ligand from Plasma

Aplastic plasma from a variety of species is known to contain activities that stimulate hematopoiesis in-vitro; however no hematopoietic stimulatory factor has previously been reported isolated from plasma. One source of aplastic plasma is that obtained from irradiated pigs. This aplastic porcine plasma (APP) stimulates human hematopoiesis in-vitro. To determine if APP contained the mpl ligand, its effect on $^3$H-thymidine incorporation into Ba/F3 cells transfected with human mpl P (Ba/F3-mpl) was measured. APP stimulated $^3$H-thymidine incorporation into Ba/F3-mpl cells but not Ba/F3 control cells (i.e. not transfected with human mpl P). No such activity was observed in normal porcine plasma. These results indicated that APP contained a factor (s) that transduces a proliferative signal through the mpl receptor and therefore may be the natural ligand for this receptor. This was further supported by the finding that soluble mpl-IgG blocked the stimulatory effects of APP on Ba/F3-mpl cells.

The activity in APP appeared to be a protein since pronase, DTT, or heat destroy the activity in APP (FIG. 1). The activity was also non-dialyzable. The activity was, however, stable to low pH (pH 2.5 for 2 hrs. ) and was shown to bind and elute from several lectin-affinity columns, indicating that it was a glycoprotein. To further elucidate the structure and identity of this activity it was affinity purified from APP.

Figure 2:
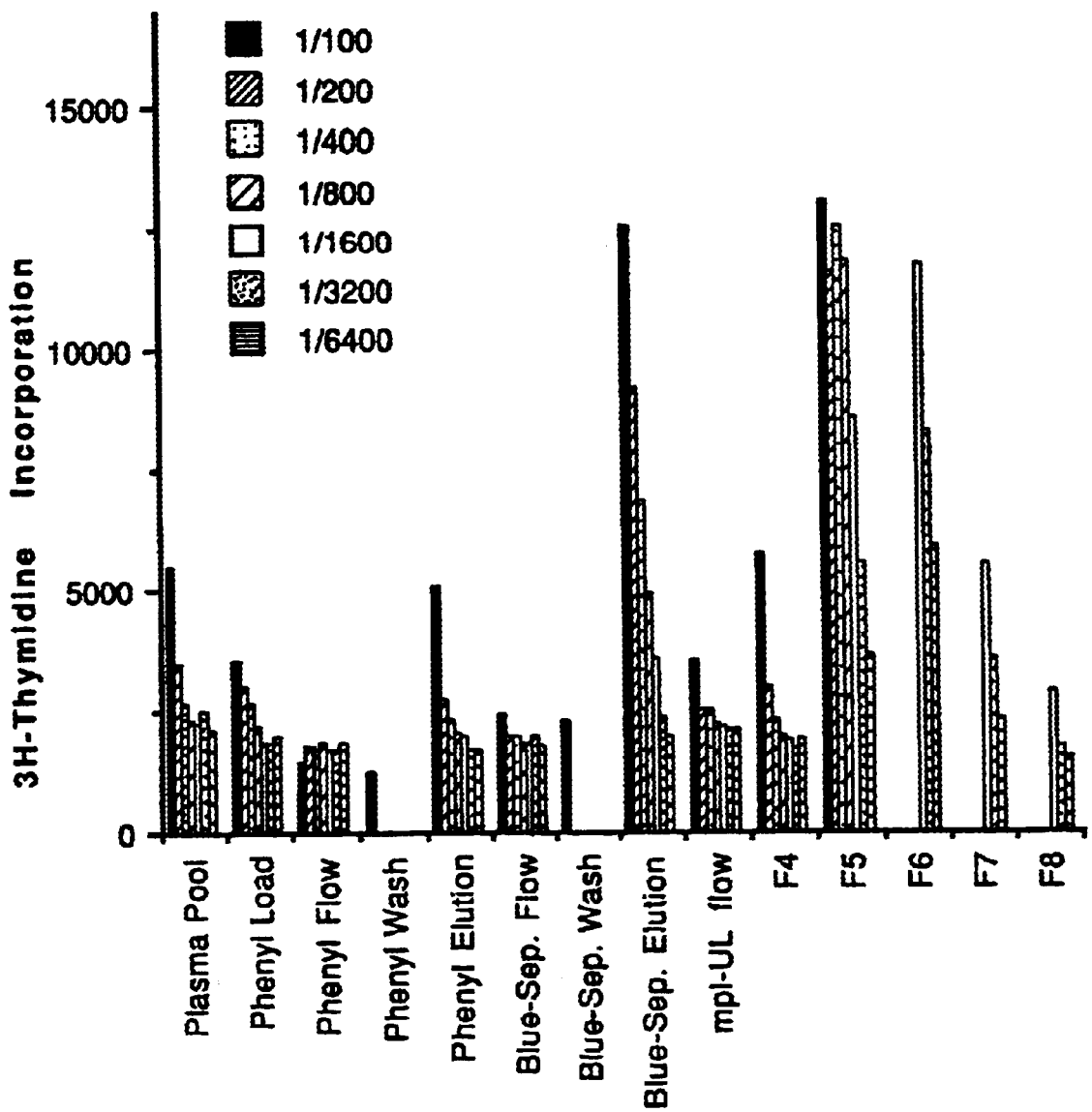
FIG. 2. Elution of mpl-ligand activity from Phenyl-Toyopearl, Blue-Sepharose and Ultralink-mpl columns. Fractions 4–8 from the mpl affinty column were the peak activity fractions eluted from the column.

5 liters of APP was purified according to the protocol in Example I. The recovery of activity from each step is shown in FIG. 2 and fold purification is provided in Table 1. The overall recovery of activity through the mpl-affinity column was approximately 10%. The peak activity fraction (F6) from the mpl-affinity column has an estimated specific activity of $9.8 \times 10^6$ units/mg. The overall purification from 5 L of APP was approximately $4 \times 10^6$ fold (0.8 units/mg to $3.3 \times 10^6$ units/mg) with a $83 \times 10^6$ fold reduction in protein (250 gms to 3 µg );

TABLE 1

Purification of mpl ligand

| Sample | Volume mls | Protein mg/ml | Units/ml | Units | Specific Activity Units/mg | Yield % | Fold Purification |
|---|---|---|---|---|---|---|---|
| APP | 5000 | 50 | 40 | 200,000 | 0.8 | — | 1 |
| Phenyl | 4700 | 0.8 | 40 | 200,000 | 50 | 94 | 62 |
| Blue-Sep. | 640 | 0.93 | 400 | 256,000 | 430 | 128 | 538 |
| mpl-UL (Fxns 5–7) | 12 | $5 \times 10^{-4}$ | 1666 | 20,000 | 3,300,000 | 10 | 4,100,000 |

Protein was determined by the Bradford assay. Protein concentration of mpl-eluted fractions 5–7 are estimates based on staining intensity of a silver stained SDS-gel. One unit is defined as that causing 50% maximal stimulation of Ba/F3-mpl cell proliferation.

Figure 3:
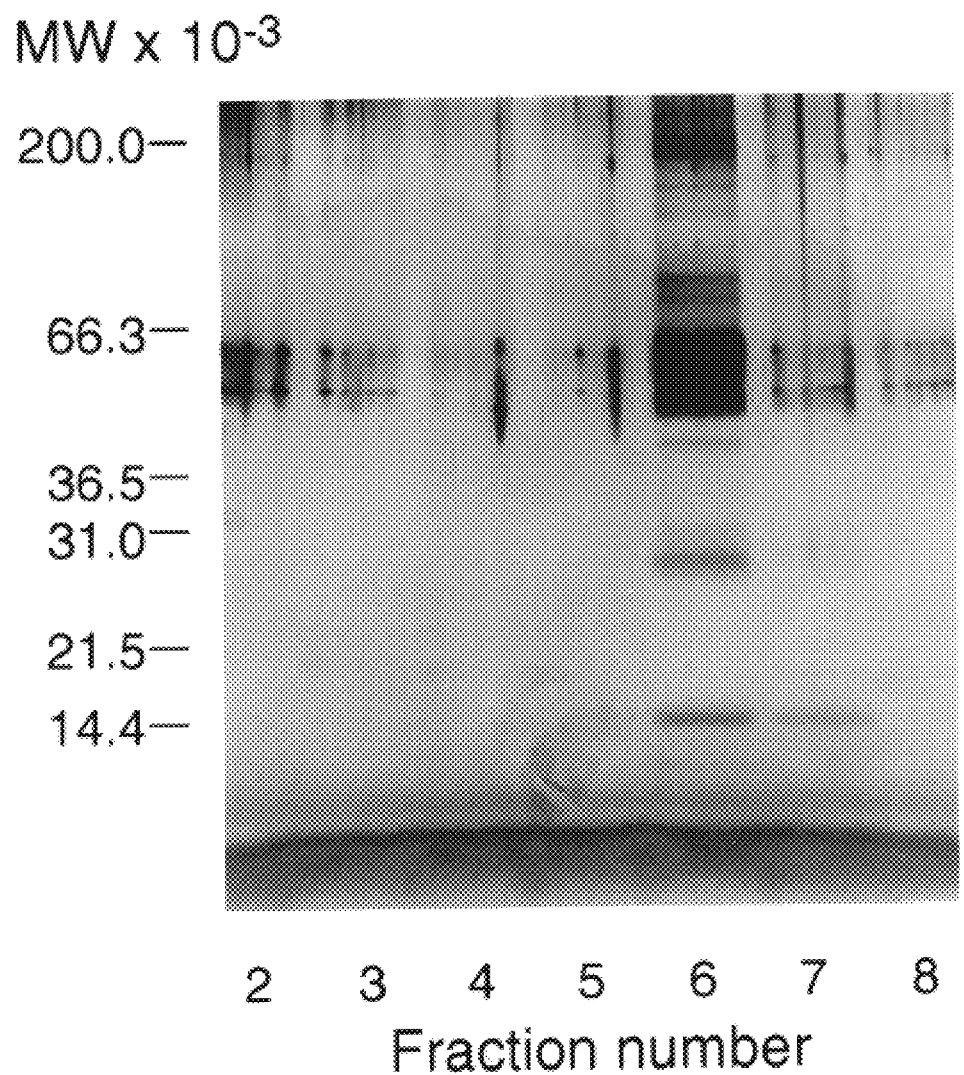
FIG. 3. SDS-PAGE of eluted Ultralink-mpl fractions. To 200 ul of each fraction 2–8, 1 ml of acetone containing 1 mM HCl at −20 C. was added. After 3 hrs. at −20 C. samples were centrifuged and resultant pellets were washed 2× with acetone at −20 C. The acetone pellets were subsequently dissolved in 30 ul of SDS-solubilization buffer, made 100 uM DTT and heated at 90 C. for 5 min. The samples were then resolved on a 4–20% SDS-polyacrlyamide gel and proteins were visualized by silver staining.

Analysis of eluted fractions from the mpl-affinity column by SDS-PAGE (4–20%, novex gel) run under reducing conditions, reveal the presence of several proteins (FIG. 3). Proteins that silver stain with the strongest intensity resolve with apparent Mr of 66,000, 55,000, 30,000, 28,000 and 14,000. To determine which of these proteins stimulate proliferation Ba/F3-mpl cell cultures these proteins were eluted from the gel as described Example II.

Figure 4:
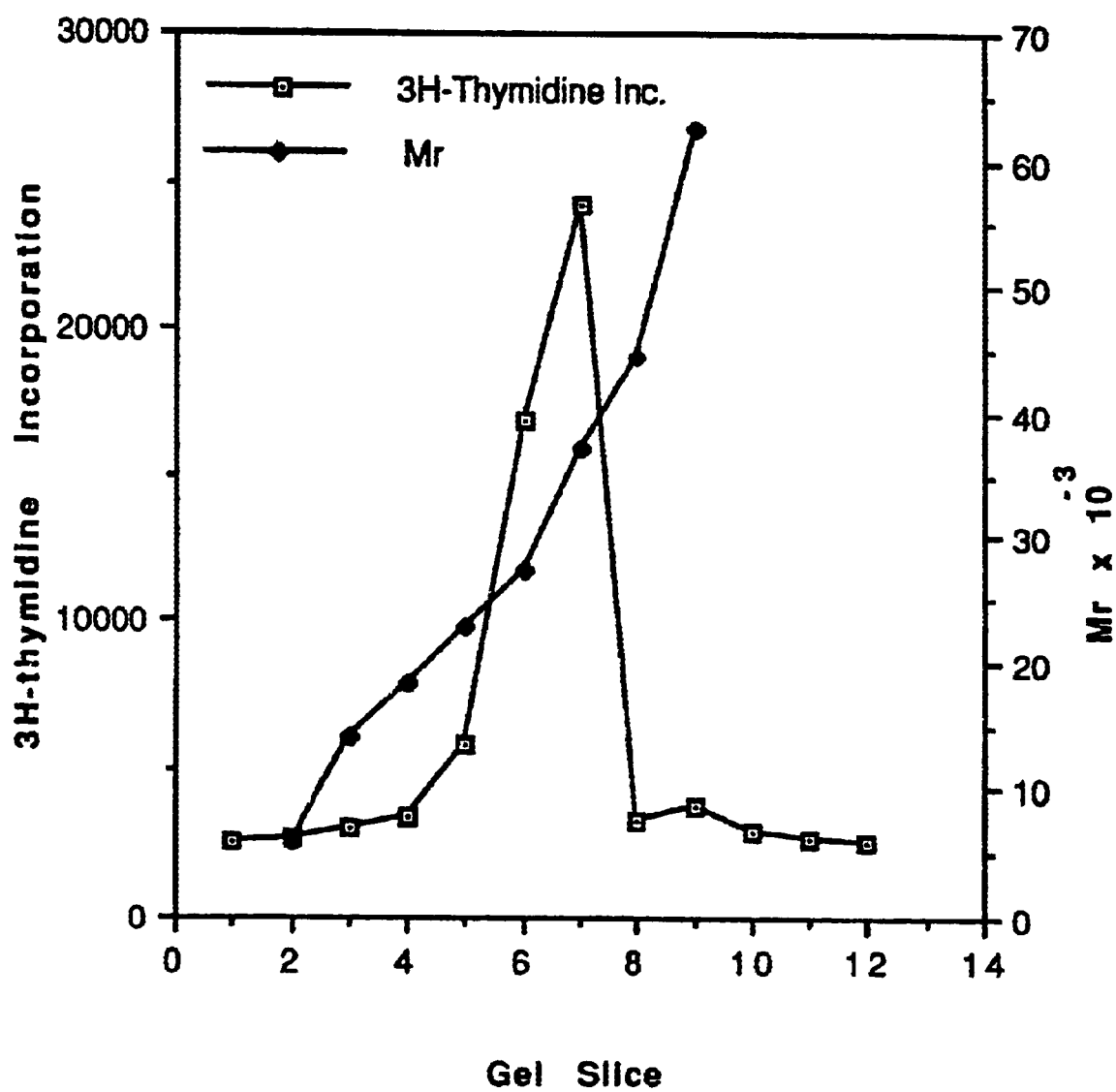
FIG. 4. Elution of mpl-ligand activity from SDS-PAGE. Fraction 6 from the mpl-affinity column was resolved on a 4–20% SDS-polyacrylamide gel under non-reducing conditions. Following electrophoresis the gel was sliced into 12 equal regions and electroeluted as described in the text. The electroeluted samples were dialyzed into PBS and assayed at a 1/20 dilution. The Mr standards used to calibrate the gel were Novex Mark 12 standards.

The results of this experiment show that most of the activity elutes from a gel slice that includes proteins with Mr 25,000–35,000, with lesser activity eluting in the 22,000–24,000 region of the gel (FIG. 4).

To identify and obtain protein sequence for the proteins resolving in this region of the gel, fraction 6 was electroblotted and sequenced as described in Example III. The only proteins that .were visable in the Mr 22,000–35,000 region of the blot had Mr of 30,000, 28,000 and 22,000.

Figure 5:
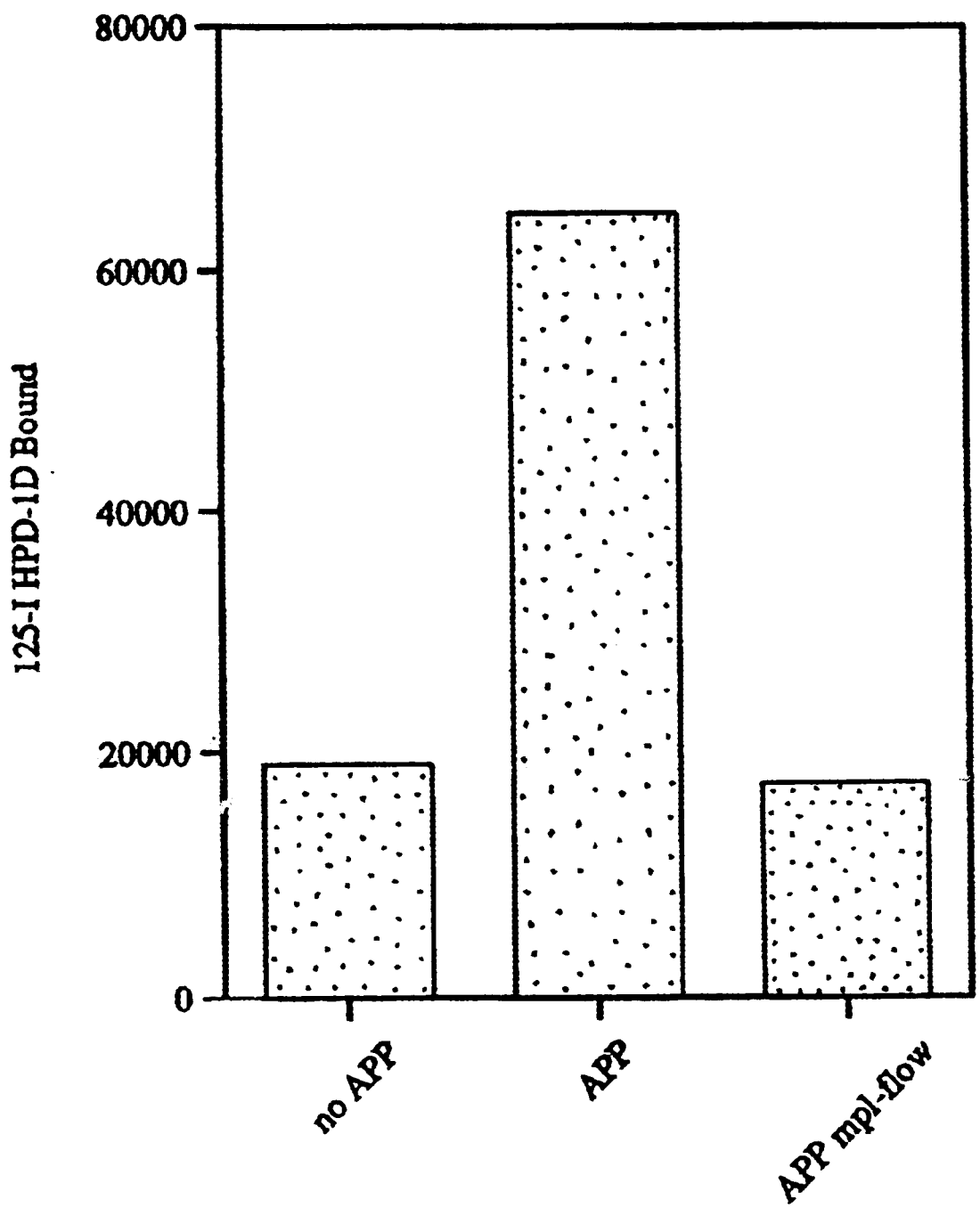
FIG. 5. Effect of mpl-ligand depleted APP on human megakaryocytopoiesis. mpl-Ligand depleted APP was made by passing 1 ml over a 1 ml mpl-affinity column (700 ug mpl-IgG/ml NHS-superose, Pharmacia). Human peripheral stem cell cultures were made 10% APP or 10% mpl-ligand depleted APP and cultured for 12 days. Megakaryocytopoiesis was quantitated as described in the text.

Bands at 30, 28 and 22 KDa were subjected to protein sequencing as described in Example IV. Protein sequences obtained were as follows:

ing the differentiation of other hemopoietic cell lineages (Methia, N et al., supra). This result suggested that the mpl receptor plays a role in the differentiation and proliferation of megakaryocytes in-vitro. To further elucidate the role of the mpl-ligand in megakaryocytopoiesis, the effects of APP and mpl-ligand depleted APP on in-vitro human megakaryocytopoiesis was compared. The effect of APP on human megakaryocytopoiesis was determined using a modification of the liquid suspension megakaryocytopoiesis assay described by Solberg et al. (Example IV). In this assay human peripheral stem cells (PSC) are treated with APP before and after mpl-IgG affinity chromatography. GP $II_bIII_a$ stimulation or megakaryocytopoiesis is quantitated with an $^{125}I$ anti-$II_bIII_a$ antibody (FIG. 5). Shown in FIG. 5 10% APP caused approximately a 3 fold stimulation while APP depleted of mpl-ligand had no effect. Significantly, the mpl-ligand depleted APP did not induce proliferation of the Ba/F3-mpl cells.

Figure 6:
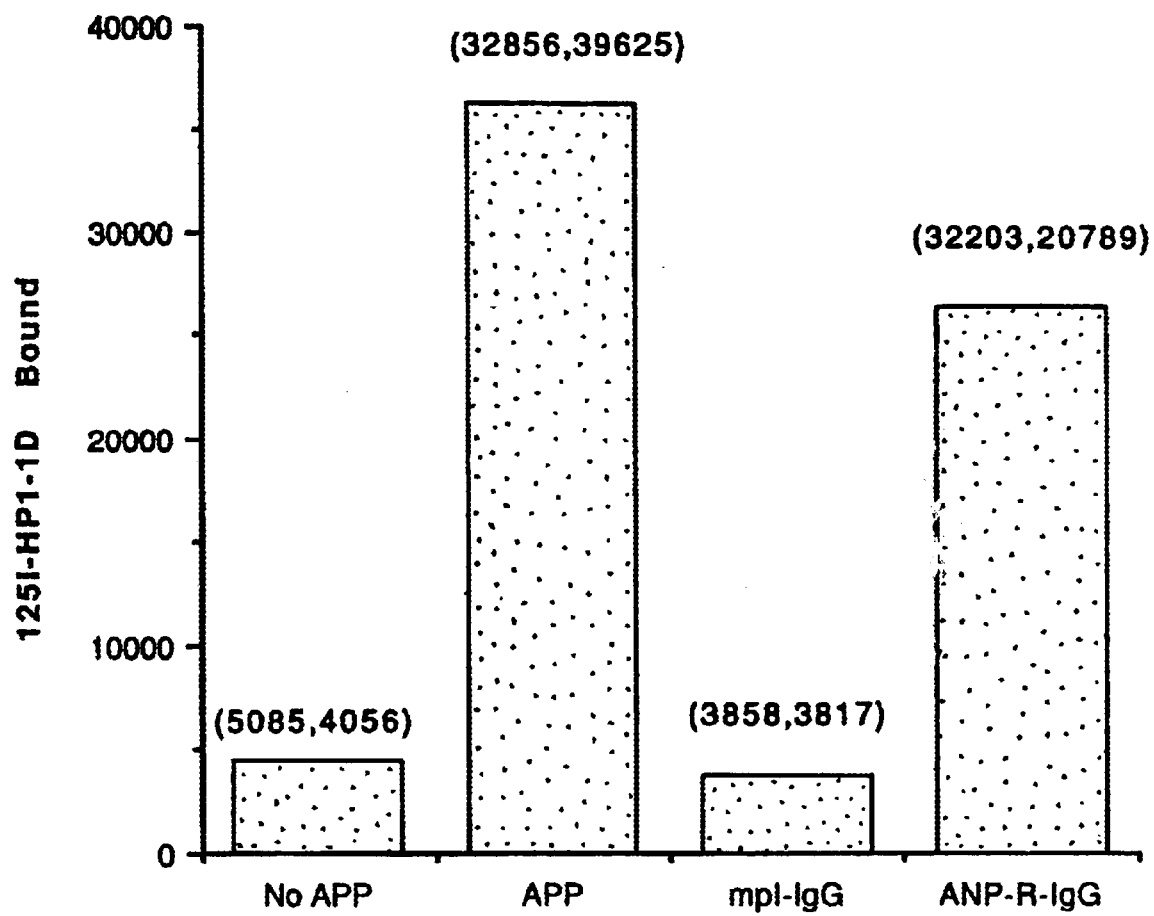
FIG. 6. Effect of mpl-IgG on the stimulation of human megakaryocytopoiesis by APP. Human peripheral stem cell cultures were made 10% with APP and cultured for 12 days. At day 0, 2 and 4, mpl-IgG (0.5 ug) or ANP-R-IgG (0.5 ug) was added. After 12 days megakaryocytopoiesis was quantitated as described in the text. The average of duplicate samples is graphed with the actual duplicate data in parenthesis.

In another experiment, soluble human mpl-IgG added at days 0, 2 and 4 to cultures containing 10% APP neutralized the stimulatory effects of APP on human megakaryocytopoiesis (FIG. 6). These results indicate that the mpl-ligand plays a role in regulating human megakaryocytopoiesis and therefore may be useful for the treatment of thrombocytopenia.

```
1) 30 KDa
 1               5              10              15              20              25
(S) P A P P A(C)D P R L L N K L L R D D (H/S) V L H (G) R L (SEQ ID NO.: 3)

2) 28 KDa
 1               5              10              15              20              25
(S) P A P P A X D P R L L N K L L R D D (H)     V L (H) G R (SEQ ID NO.: 4)

3) 22 KDa
 1         5              10
X P A P P A X D P R L X (N) (K) (SEQ ID NO.: 5)
```

Computer-assisted analysis revealed that these sequences were novel . The fact that these were the only sequences obtained indicates that the 30 KDa, 28 KDa and 22 kDa proteins are related and may be different forms of the same novel protein. Futhermore this protein(s) is a likely candidate as the natural mpl-ligand since the activity resolved on SDS-PAGE in the same region of a 4–20% gel (22,000–35,000). Futhermore the partially purified ligand migrates with a Mr of 17,000–30,000 when subjected to gel filtration chromatography using a Superose 12 (Pharmacia) column. The different Mr forms of the ligand are likely a result of proteolysis or glycosylation differences or other post or pre-translational modifications.

As described earlier, antisense human mpl RNA abrogated megakaryocytopoiesis in human bone marrow cultures enriched with CD 34+ progenitor cells without affect- 2. Additional Methods for Measurement of Thrombopoeitic activity In addition to the methods described immediately above, thrombopoeitic activity may be measured in various assays including an in-vivo mouse platelet rebound synthesis assay, induction of platelet cell surface antigen assay as measured by an anti-platelet immunoassay (anti-GPII$_b$III$_a$) for a human leukaemia megakaryoblastic cell line (CMK)(see Sato, T., et al., Brit. J. Heamatol. 72:184–190 (1989)), and induction of polyploidization in a megakaryoblastic cell line(DAMI) (see Ogura, M., et al., Blood 72(1):49–60 (1988). Maturation of megakaryocytes from immature, largely non-DNA synthesizing cells, to morphologically identifiable megakaryocytes involves a process that includes appearance of cytoplasmic organelles, acquisition of membrane antigens (GPII$_b$III$_a$), endoreplication and release of platelets as described in the background. A lineage specific promoter (i.e. the mpl ligand) of megakaryocyte maturation, would be expected to induce at least some of these changes in immature megakaryocytes leading to platelet release and alleviation of thympocytopenia. Thus, assays were designed to measure the emergence of these parameters in immature megakaryocyte cell lines, i.e. CMK and DAMI cells. The CMK assay (Example VI) measures the appearance of a specific platelet marker, $GPII_bIII_a$, and platelet shedding. The DAMI assay (Example VII) measures endoreplication since increases in ploidy are hallmarks of mature megakaryocytes. Recognizable megakaryocytes have ploidy values of 2N, 4N, 8N, 16N, 32N, etc. Finally, the in vivo assay (Example VIII) are useful in demonstrating that administration of the test compound (here the mpl ligand) results in elevation of platelet numbers.

3. Recombinant Preparation of Mpl Ligand

Preferably mpl ligand is prepared by standard recombinant procedures which involves production of the mpl ligand polypeptide by culturing cells transfected to express mpl ligand nucleic acid (typically by transforming the cells with an expression vector) and recovering the polypeptide from the cells. However, it is optionally envisioned that the mpl ligand may be produced by homologous recombination, or with recombinant production methods utilizing control elements introduced into cells already containing DNA encoding the mpl ligand. For example, a powerful promoter/enhancer element, a suppressor, or an exogenous transcription modulatory element may be inserted in the genome of the intended host cell in proximity and orientation sufficient to influence the transcription of DNA encoding the desired mpl ligand polypeptide. The control element does not encode the mpl ligand, rather the DNA is indigenous to the host cell genome. One next screens for cells making the receptor polypeptide of this invention, or for increased or decreased levels of expression, as desired.

Thus, the invention contemplates a method for producing mpl ligand comprising inserting into the genome of a cell containing the mpl ligand nucleic acid molecule a transcription modulatory element in sufficient proximity and orientation to the nucleic acid molecule to influence transcription thereof, with an optional further step comprising culturing the cell containing the transcription modulatory element and the nucleic acid molecule. The invention also contemplates a host cell containing the indigenous mpl ligand nucleic acid molecule operably linked to exogenous control sequences recognized by the host cell.

A. Isolation of DNA Encoding mpl Ligand Polypeptide

The DNA encoding mpl ligand polypeptide may be obtained from any cDNA library prepared from tissue believed to possess the mpl ligand mRNA and to express it at a detectable level. The mpl ligand gene may also be obtained from a genomic DNA library or by in vitro oligonucleotide synthesis from the complete nucleotide or amino acid sequence.

Libraries are screened with probes designed to identify the gene of interest or the protein encoded by it. For cDNA expression libraries, suitable probes include monoclonal or polyclonal antibodies that recognize and specifically bind to the mpl ligand. For cDNA libraries suitable probes include oligonucleotides of about 20–80 bases in length that encode known or suspected portions of the mpl ligand cDNA from the same or different species; and/or complementary or homologous cDNAs or fragments thereof that encode the same or a similar gene. Appropriate probes for screening genomic DNA libraries include, but are not limited to, oligonucleotides, cDNAs, or fragments thereof that encode the same or a similar gene, and/or homologous genomic DNAs or fragments thereof. Screening the cDNA or genomic library with the selected probe may be conducted using standard procedures as described in chapters 10–12 of Sambrook et al., supra.

An alternative means to isolate the gene encoding mpl ligand is to use PCR methodology as described in section 14 of Sambrook et al., supra. This method requires the use of oligonucleotide probes that will hybridize to DNA encoding the mpl ligand. Strategies for selection of oligonucleotides are described below.

A preferred method of practicing this invention is to use carefully selected oligonucleotide sequences to screen cDNA libraries from various tissues, preferably porcine kidney cell lines. Optionally, human kidney cell line cDNA libraries are screened with the oligonucleotide probes. Alternatively, human genomic libraries may be screened with the oligonucleotide probes.

The oligonucleotide sequences selected as probes should be of sufficient length and sufficiently unambiguous that false positives are minimized. The actual nucleotide sequence(s) is usually designed based on regions of the mpl ligand which have the least codon redundancy. The oligonucleotides may be degenerate at one or more positions. The use of degenerate oligonucleotides is of particular importance where a library is screened from a species in which preferential codon usage is not known.

The oligonucleotide must be labeled such that it can be detected upon hybridization to DNA in the library being screened. The preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the mpl ligand nucleic acid that encodes a full-length mpl ligand polypeptide. In some preferred embodiments, the nucleic acid sequence includes the native mpl ligand signal sequence. Nucleic acid having all the protein coding sequence is obtained by screening selected cDNA or genomic libraries using the deduced amino acid sequence.

B. Amino Acid Sequence Variants of Native mpl Ligand

Amino acid sequence variants of mpl ligand are prepared by introducing appropriate nucleotide changes into the mpl ligand DNA, or by in vitro synthesis of the desired mpl ligand polypeptide. Such variants include, for example, deletions from, or insertions or substitutions of, residues within the amino acid sequence for the porcine mpl ligand. Any combination of deletion, insertion, and substitution is made to arrive at the final construct, provided that the final construct possesses the desired characteristics. The amino acid changes also may alter post-translational processes of the mpl ligand, such as changing the number or position of glycosylation sites.

For the design of amino acid sequence variants of the mpl ligand, the location of the mutation site and the nature of the mutation will depend on the mpl ligand characteristic(s) to be modified. The sites for mutation can be modified individually or in series, e.g., by (1) substituting first with conservative amino acid choices and then with more radical selections depending upon the results achieved, (2) deleting the target residue, or (3) inserting residues of the same or a different class adjacent to the located site, or combinations of options 1–3.

A useful method for identification of certain residues or regions of the mpl ligand polypeptide that are preferred locations for mutagenesis is called "alanine scanning mutagenesis," as described by Cunningham and Wells, *Science*, 244:1081–1085 (1989). Here, a residue or group of target residues are identified (e.g., charged residues such as arg, asp, his, lys, and glu) and replaced by any but preferably a neutral or negatively charged amino acid (most preferably alanine or polyalanine) to affect the interaction of the amino acids with the surrounding aqueous environment in or outside the cell. Those domains demonstrating functional sensitivity to the substitutions then are refined by introducing further or other variants at or for the sites of substitution. Thus, while the site for introducing an amino acid sequence variation is predetermined, the nature of the mutation per se need not be predetermined. For example, to optimize the performance of a mutation at a given site, ala scanning or random mutagenesis is conducted at the target codon or region and the expressed mpl ligand variants are screened for the optimal combination of desired activity.

There are two principal variables in the construction of amino acid sequence variants: the location of the mutation site and the nature of the mutation. For example, variants of the mpl ligand polypeptide include variants from the mpl ligand sequence, and may represent naturally occurring alleles (which will not require manipulation of the mpl ligand DNA) or predetermined mutant. forms made by mutating the DNA, either to arrive at an allele or a variant not found in nature. In general, the location and nature of the mutation chosen will depend upon the mpl ligand characteristic to be modified.

Amino acid sequence deletions generally range from about 1 to 30 residues, more preferably, about 1 to 10 residues, and typically are contiguous. Contiguous deletions ordinarily are made in even numbers of residues, but single or odd numbers of deletions are within the scope hereof. Deletions may be introduced into regions of low homology among the mpl ligands that share the most sequence identity to modify the activity of the mpl ligand. Or deletions may be introduced into regions of low homology among human mpl ligand and other mamalian mpl ligand polypeptides that share the most sequence identity to the human mpl ligand. Deletions from a mammalian mpl ligand polypeptide in areas of substantial homology with other mammalian mpl ligands will be more likely to modify the biological activity of the mpl ligand more significantly. The number of consecutive deletions will be selected so as to preserve the tertiary structure of mpl ligands in the affected domain, e.g., beta-pleated sheet or alpha helix.

Amino acid sequence insertions include amino- and/or carboxyl-terminal fusions ranging in length from one residue to polypeptides containing a hundred or more residues, as well as intrasequence insertions of single or multiple amino acid residues. Intrasequence insertions (i.e., insertions within the mature mpl ligand sequence) may range generally from about 1 to 10 residues, more preferably 1 to 5, most preferably 1 to 3. An exemplary preferred fusion is that of mpl ligand or fragment thereof and another cytokine or fragment thereof. Insertions are often made in even numbers of residues, but this is not required. Examples of terminal insertions include mature mpl ligand with an N-terminal methionyl residue, an artifact of the direct expression of mature mpl ligand in recombinant cell culture, and fusion of a heterologous N-terminal signal sequence to the N-terminus of the mature mpl ligand molecule to facilitate the secretion of mature mpl ligand from recombinant hosts. Such signal sequences generally will be obtained from, and thus homologous to, the intended host cell species. Suitable sequences include STII or Ipp for *E. coli*, alpha factor for yeast, and viral signals such as herpes gD for mammalian cells.

Other insertional variants of the mpl ligand molecule include the fusion to the N- or C-terminus of mpl ligand of immunogenic polypeptides (i.e., not endogenous to the host to which the fusion is administered), e.g., bacterial polypeptides such as beta-lactamase or an enzyme encoded by the *E. coli* trp locus, or yeast protein, and C-terminal fusions with proteins having a long half-life such as immunoglobulin constant regions (or other immunoglobulin regions), albumin, or ferritin, as described in WO 89/02922 published Apr. 6, 1989.

A third group of variants are amino acid substitution variants. These variants have at least one amino acid residue in the mpl ligand molecule removed and a different residue inserted in its place. The sites of greatest interest for substitutional mutagenesis include sites identified as the active site(s) of mpl ligand and sites where the amino acids found in other analogues are substantially different in terms of side-chain bulk, charge, or hydrophobicity, but where there is also a high degree of sequence identity at the selected site among various mpl ligand species and/or within the various animal analogues of one mpl ligand member.

Other sites of interest are those in which particular residues of the mpl ligand obtained from various family members and/or animal species within one member are identical. These sites, especially those falling within a sequence of at least three other identically conserved sites, are substituted in a relatively conservative manner. Such conservative substitutions are shown in Table 2 under the heading of preferred substitutions. If such substitutions result in a change in biological activity, then more substantial changes, denominated exemplary substitutions in Table 2, or as further described below in reference to amino acid classes, are introduced and the products screened.

TABLE 2

| Original Residue | Exemplary Substitutions | Preferred Substitutions |
| --- | --- | --- |
| Ala (A) | val; leu; ile | val |
| Arg (R) | lys; gln; asn | lys |
| Asn (N) | gln; his; lys; arg | gln |
| Asp (D) | glu | glu |
| Cys (C) | ser | ser |
| Gln (Q) | asn | asn |
| Glu (E) | asp | asp |
| Gly (G) | pro | pro |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala | leu |
| Pro (P) | gly | gly |
| Ser (S) | thr | thr |
| Thr (T) | ser | ser |
| Trp (W) | tyr | tyr |
| Tyr (Y) | trp; phe; thr; ser | phe |
| Val (V) | ile; leu; met; phe; ala; norleucine | leu |

Substantial modifications in function or immunological identity of the mpl ligand are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;

(2) neutral hydrophilic: cys, ser, thr;

(3) acidic: asp, glu;

(4) basic: asn, gln, his, lys, arg;

(5) residues that influence chain orientation: gly, pro; and (6) aromatic: trp, tyr, phe.

Non-conservative substitutions will entail exchanging a member of one of these classes for another. Such substituted residues also may be introduced into the conservative substitution sites or, more preferably, into the remaining (non-conserved) sites.

In one embodiment of the invention, it is desirable to inactivate one or more protease cleavage sites that are present in the molecule. These sites are identified by inspection of the encoded amino acid sequence, in the case of trypsin, e.g., for an arginyl or lysinyl residue. When protease cleavage sites are identified, they are rendered inactive by proteolytic cleavage by substituting the targeted residue with another residue, preferably a basic residue such as glutamine or a hydrophobic residue such as serine; by deleting the residue; or by inserting a prolyl residue immediately after the residue.

In another embodiment, any methionyl residues other than the starting methionyl residue of the signal sequence, or any residue located within about three residues N- or C-terminal to each such methionyl residue, is substituted by another residue (preferably in accord with Table 2) or deleted. Alternatively, about 1–3 residues are inserted adjacent to such sites.

Any cysteine residues not involved in maintaining the proper conformation of the mpl ligand also may be substituted, generally with serine, to improve the oxidative stability of the molecule and prevent aberrant crosslinking.

Nucleic acid molecules encoding amino acid sequence variants of mpl ligand are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of mpl ligand polypeptide.

Oligonucleotide-mediated mutagenesis is a preferred method for preparing substitution, deletion, and insertion variants of mpl ligand DNA. This technique is well known in the art as described by Adelman et al., *DNA*, 2:183 (1983). Briefly, mpl ligand DNA is altered by hybridizing an oligonucleotide encoding the desired mutation to a DNA template, where the template is the single-stranded form of a plasmid or bacteriophage containing the unaltered or native DNA sequence of mpl ligand. After hybridization, a DNA polymerase is used to synthesize an entire second complementary strand of the template that will thus incorporate the oligonucleotide primer, and will code for the selected alteration in the mpl ligand DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Nat. Acad. Sci. USA*, 75:5765 (1978).

The DNA template can be generated by those vectors that are either derived from bacteriophage M13 vectors (the commercially available M13 mp 18 and M13 mp 19 vectors are suitable), or those vectors that contain a single-stranded phage origin of replication as described by Viera et al. *Meth. Enzymol.*, 153:3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, NY 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of the mpl ligand, and the other strand (the original template) encodes the native, unaltered sequence of the mpl ligand. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector for protein production, generally an expression vector of the type typically employed for transformation of an appropriate host.

The method described immediately above may be modified such that a homoduplex molecule is created wherein both strands of the plasmid contain the mutation(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thio-deoxyribocytosine called dCTP-(aS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101, as described above.

DNA encoding mpl ligand mutants with more than one amino acid to be substituted may be generated in one of several ways. If the amino acids are located close together in the polypeptide chain, they may be mutated simultaneously using one oligonucleotide that codes for all of the desired amino acid substitutions. If, however, the amino acids are located some distance from each other (separated by more than about ten amino acids), it is more difficult to generate a single oligonucleotide that encodes all of the desired changes. Instead, one of two alternative methods may be employed.

In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions.

The alternative method involves two or more rounds of mutagenesis to produce the desired mutant. The first round is as described for the single mutants: wild-type DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on. PCR mutagenesis is also suitable for making amino acid variants of mpl ligand polypeptide. While the following discussion refers to DNA, it is understood that the technique also finds application with RNA. The PCR technique generally refers to the following procedure (see Erlich, supra, the chapter by R. Higuchi, p. 61–70): When small amounts of template DNA are used as starting material in a PCR, primers that differ slightly in sequence from the corresponding region in a template DNA can be used to generate relatively large quantities of a specific DNA fragment that differs from the template sequence only at the positions where the primers differ from the template. For introduction of a mutation into a plasmid DNA, one of the primers is designed to overlap the position of the mutation and to contain the mutation; the sequence of the other primer must be identical to a stretch of sequence of the opposite strand of the plasmid, but this sequence can be located anywhere along the plasmid DNA. It is preferred, however, that the sequence of the second primer is located within 200 nucleotides from that of the first, such that in the end the entire amplified region of DNA bounded by the primers can be easily sequenced. PCR amplification using a primer pair like the one just described results in a population of DNA fragments that differ at the position of the mutation specified by the primer, and possibly at other positions, as template copying is somewhat error-prone.

If the ratio of template to product material is extremely low, the vast majority of product DNA fragments incorporate the desired mutation(s). This product material is used to replace the corresponding region in the plasmid that served as PCR template using standard DNA technology. Mutations at separate positions can be introduced simultaneously by either using a mutant second primer, or performing a second PCR with different mutant primers and ligating the two resulting PCR fragments simultaneously to the vector fragment in a three (or more)-part ligation.

In a specific example of PCR mutagenesis, template plasmid DNA (1 µg) is linearized by digestion with a restriction endonuclease that has a unique recognition site in the plasmid DNA outside of the region to be amplified. Of this material, 100 ng is added to a PCR mixture containing PCR buffer, which contains the four deoxynucleotide triphosphates and is included in the GeneAmp® kits (obtained from Perkin-Elmer Cetus, Norwalk, Conn. and Emeryville, Calif.), and 25 pmole of each oligonucleotide primer, to a final volume of 50 µl. The reaction mixture is overlayed with 35 µl mineral oil. The reaction mixture is denatured for five minutes at 100° C., placed briefly on ice, and then 1 µl Thermus aquaticus (Taq) DNA polymerase (5 units/µl, purchased from Perkin-Elmer Cetus) is added below the mineral oil layer. The reaction mixture is then inserted into a DNA Thermal Cycler (purchased from Perkin-Elmer Cetus) programmed as follows:

2 min. 55° C.
30 sec. 72° C., then 19 cycles of the following:
30 sec. 94° C.
30 sec. 55° C., and
30 sec. 72° C.

At the end of the program, the reaction vial is removed from the thermal cycler and the aqueous phase transferred to a new vial, extracted with phenol/chloroform (50:50 vol), and ethanol precipitated, and the DNA is recovered by standard procedures. This material is subsequently subjected to the appropriate treatments for insertion into a vector.

Another method for preparing variants, cassette mutagenesis, is based on the technique described by Wells, et al., *Gene,* 34:315 (1985). The starting material is the plasmid (or other vector) comprising the mpl ligand DNA to be mutated. The codon(s) in the mpl ligand DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the mpl ligand DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are compatible with the ends of the linearized plasmid, such that it can be directly ligated to the plasmid. This plasmid now contains the mutated mpl ligand DNA sequence.

C. Insertion of Nucleic Acid into a Replicable Vector

The nucleic acid (e.g., cDNA or genomic DNA) encoding native or variant mpl ligand polypeptide is inserted into a replicable vector for further cloning (amplification of the DNA) or for expression. Many vectors are available, and selection of the appropriate vector will depend on 1) whether it is to be used for DNA amplification or for DNA expression, 2) the size of the nucleic acid to be inserted into the vector, and 3) the host cell to be transformed with the vector. Each vector contains various components depending on its function (amplification of DNA or expression of DNA) and the host cell with which it is compatible. The vector components generally include, but are not limited to, one or more of the following: a signal sequence, an origin of replication, one or more marker genes, an enhancer element, a promoter, and a transcription termination sequence.

(i) Signal Sequence Component

The mpl ligand of this invention may be expressed not only directly, but also as a fusion with a heterologous polypeptide, preferably a signal sequence or other polypeptide having a specific cleavage site at the N-terminus of the mature protein or polypeptide. In general, the signal sequence may be a component of the vector, or it may be a part of the mpl ligand DNA that is inserted into the vector.

The heterologous signal sequence selected should be one that is recognized and processed (i.e., cleaved by a signal peptidase) by the host cell. For prokaryotic host cells that do not recognize and process the native mpl ligand signal sequence, the signal sequence is substituted by a prokaryotic signal sequence selected, for example, from the group of the alkaline phosphatase, penicillinase, lpp, or heat-stable enterotoxin II leaders. For yeast secretion the native signal sequence may be substituted by, e.g., the yeast invertase, alpha factor, or acid phosphatase leaders, the *C. albicans* glucoamylase leader (EP 362,179 published Apr. 4, 1990), or the signal described in WO 90/13646 published Nov. 15, 1990. In mammalian cell expression the native signal sequence (i.e., the mpl ligand presequence that normally directs secretion of mpl ligand from its naitve mammalian cells in vivo) is satisfactory, although other mammalian signal sequences may be suitable, such as signal sequences from other mpl ligand polypeptides or from the same mpl ligand from a different animal species, signal sequences from a mpl ligand, and signal sequences from secreted polypeptides of the same or related species, as well as viral secretory leaders, for example, the herpes simplex gD signal.

(ii) Origin of Replication Component

Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the $2\mu$ plasmid origin is suitable for yeast, and various viral origins (SV40, polyoma, adenovirus, VSV or BPV) are useful for cloning vectors in mammalian cells. Generally, the origin of replication component is not needed for mammalian expression vectors (the SV40 origin may typically be used only because it contains the early promoter).

Most expression vectors are "shuttle" vectors, i.e., they are capable of replication in at least one class of organisms but can be transfected into another organism for expression. For example, a vector is cloned in *E. coli* and then the same vector is transfected into yeast or mammalian cells for expression even though it is not capable of replicating independently of the host cell chromosome.

DNA may also be amplified by insertion into the host genome. This is readily accomplished using Bacillus species as hosts, for example, by including in the vector a DNA sequence that is complementary to a sequence found in Bacillus genomic DNA. Transfection of Bacillus with this vector results in homologous recombination with the genome and insertion of mpl ligand DNA. However, the recovery of genomic DNA encoding mpl ligand is more complex than that of an exogenously replicated vector because restriction enzyme digestion is required to excise the mpl ligand DNA.

(iii) Selection Gene Component

Expression and cloning vectors should contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli.

One example of a selection scheme utilizes a drug to arrest growth of a host cell. Those cells that are successfully transformed with a heterologous gene express a protein conferring drug resistance and thus survive the selection regimen. Examples of such dominant selection use the drugs neomycin Southern et al (*J. Molec. Appl. Genet.*, 1: 327 [1982]) mycophenolic acid Mulligan et al (*Science*, 209:1422 [1980]) or hygromycin (Sugden et al, *Mol. Cell. Biol.*, 5: 410–413 [1985]). The three examples given above employ bacterial genes under eukaryotic control to convey resistance to the appropriate drug G418 or neomycin (geneticin), xgpt (mycophenolic acid), or hygromycin, respectively.

Another example of suitable selectable markers for mammalian cells are those that enable the identification of cells competent to take up the mpl ligand nucleic acid, such as dihydrofolate reductase (DHFR) or thymidine kinase. The mammalian cell transformants are placed under selection pressure that only the transformants are uniquely adapted to survive by virtue of having taken up the marker. Selection pressure is imposed by culturing the transformants under conditions in which the concentration of selection agent in the medium is successively changed, thereby leading to amplification of both the selection gene and the DNA that encodes mpl ligand polypeptide. Amplification is the process by which genes in greater demand for the production of a protein critical for growth are reiterated in tandem within the chromosomes of successive generations of recombinant cells. Increased quantities of mpl ligand are synthesized from the amplified DNA.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity, prepared and propagated as described by Urlaub and Chasin, *Proc. Natl. Acad. Sci. USA*, 77:4216 [1980]. The transformed cells are then exposed to increased levels of Mtx. This leads to the synthesis of multiple copies of the DHFR gene, and, concomitantly, multiple copies of other DNA comprising the expression vectors, such as the DNA encoding mpl ligand. This amplification technique can be used with any otherwise suitable host, e.g., ATCC No. CCL61 CHO-K1, notwithstanding the presence of endogenous DHFR if, for example. a mutant DHFR gene that is highly resistant to Mtx is employed (EP 117,060). Alternatively, host cells [particularly wild-type hosts that contain endogenous DHFR] transformed or co-transformed with DNA sequences encoding mpl ligand, wild-type DHFR protein, and another selectable marker such as aminoglycoside 3' phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

A suitable selection gene for use in yeast is the trp1 gene present in the yeast plasmid YRp7 (Stinchcomb et al., *Nature*, 282:39 [1979]; Kingsman et al., *Gene*, 7:141 [1979]; or Tschemper et al., *Gene*, 10: 157 [1980]). The trp1 gene provides a selection marker for a mutant strain of yeast lacking the ability to grow in tryptophan, for example, ATCC No. 44076 or PEP4-1 (Jones, *Genetics*, 85: 12 [1977]). The presence of the trp1 lesion in the yeast host cell genome then provides an effective environment for detecting transformation by growth in the absence of tryptophan.

Similarly, Leu2-deficient yeast strains (ATCC 20,622 or 38,626) are complemented by known plasmids bearing the Leu2 gene.

(iv) Promoter Component

Expression and cloning vectors usually contain a promoter that is recognized by the host organism and is operably linked to the mpl ligand nucleic acid. Promoters are untranslated sequences located upstream (5') to the start codon of a structural gene (generally within about 100 to 1000 bp) that control the transcription and translation of particular nucleic acid sequence, such as the mpl ligand nucleic acid sequence, to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. At this time a large number of promoters recognized by a variety of potential host cells are well known. These promoters are operably linked to mpl ligand encoding DNA by removing the promoter from the source DNA by restriction enzyme digestion and inserting the isolated promoter sequence into the vector. Both the native mpl ligand promoter sequence and many heterologous promoters may be used to direct amplification and/or expression of the mpl ligand DNA. However, heterologous promoters are preferred, as they generally permit greater transcription and higher yields of expressed mpl ligand as compared to the native mpl ligand promoter.

Promoters suitable for use with prokaryotic hosts include the β-lactamase and lactose promoter systems (Chang et al., *Nature*, 275:615 [1978]; and Goeddel et al., *Nature*, 281: 544 [1979]), alkaline phosphatase, a tryptophan (trp) promoter system (Goeddel, *Nucleic Acids Res.*, 8:4057 [1980] and EP 36,776) and hybrid promoters such as the tac promoter (deBoer et al., *Proc. Natl. Acad. Sci. USA*, 80:21–25 [1983]). However, other known bacterial promoters are suitable. Their nucleotide sequences have been published, thereby enabling a skilled worker operably to ligate them to DNA encoding mpl ligand (Siebenlist et al., *Cell*, 20:269 [1980]) using linkers or adaptors to supply any required restriction sites. Promoters for use in bacterial systems also will contain a Shine-Dalgarno (S.D.) sequence operably linked to the DNA encoding mpl ligand polypeptide.

Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CXCAAT region where X may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase (Hitzeman et al., *J. Biol. Chem.*, 255:2073 [1980]) or other glycolytic enzymes (Hess et al., *J. Adv. Enzyme Reg.*, 7:149 [1968]; and Holland, *Biochemistry*, 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, met allothionein, glyceraldehyde-3-phosphate dehydrogenase, and enzymes responsible for maltose and galactose utilization. Suitable vectors and promoters for use in yeast expression are further described in Hitzeman et al., EP 73,657A. Yeast enhancers also are advantageously used with yeast promoters.

Mpl ligand transcription from vectors in mammalian host cells is controlled, for example, by promoters obtained from the genomes of viruses such as polyoma virus, fowlpox virus (UK 2,211,504 published Jul. 5, 1989), adenovirus (such as Adenovirus 2), bovine papilloma virus, avian sarcoma virus, cytomegalovirus, a retrovirus hepatitis-B virus and most preferably Simian Virus 40 (SV40), from heterologous mammalian promoters, e.g., the actin promoter or an immunoglobulin promoter, from heat-shock promoters, and from the promoter normally associated with the mpl ligand sequence, provided such promoters are compatible with the host cell systems.

The early and late promoters of the SV40 virus are conveniently obtained as an SV40 restriction fragment that also contains the SV40 viral origin of replication. Fiers et al., *Nature*, 273:113 (1978); Mulligan and Berg, *Science*, 209:1422–1427 (1980); Pavlakis et al., *Proc. Natl. Acad. Sci. USA*, 78:7398–7402 (1981). The immediate early promoter of the human cytomegalovirus is conveniently obtained as a HindIII E restriction fragment. Greenaway et al., *Gene*, 18:355–360 (1982). A system for expressing DNA in mammalian hosts using the bovine papilloma virus as a vector is disclosed in U.S. Pat. No. 4,419,446. A modification of this system is described in U.S. Pat. No. 4,601,978. See also Gray et al., *Nature*, 295:503–508 (1982) on expressing cDNA encoding immune interferon in monkey cells; Reyes et al., *Nature*, 297:598–601 (1982) on expression of human β-interferon cDNA in mouse cells under the control of a thymidine kinase promoter from herpes simplex virus; Canaani and Berg, *Proc. Natl. Acad. Sci. USA*, 79: 5166–5170 (1982) on expression of the human interferon β1 gene in cultured mouse and rabbit cells; and Gorman et al., *Proc. Natl. Acad. Sci. USA*, 79: 6777–6781 (1982) on expression of bacterial CAT sequences in CV-1 monkey kidney cells, chicken embryo fibroblasts, Chinese hamster ovary cells, HeLa cells, and mouse NIH-3T3 cells using the Rous sarcoma virus long terminal repeat as a promoter.

(v) Enhancer Element Component

Transcription of a DNA encoding the mpl ligand of this invention by higher eukaryotes is often increased by inserting an enhancer sequence into the vector. Enhancers are cis-acting elements of DNA, usually about from 10 to 300 bp, that act on a promoter to increase its transcription. Enhancers are relatively orientation and position independent, having been found 5' (Laimins et al. *Proc. Natl. Acad. Sci. USA*, 78:993 [1981]) and 3' (Lusky et al. *Mol. Cell Bio.*, 3:1108 [1983]) to the transcription unit, within an intron (Banerji et al. *Cell*, 33:729 [1983]), as well as within the coding sequence itself (Osborne et al. *Mol. Cell Bio.*, 4:1293 [1984]). Many enhancer sequences are now known from mammalian genes (globin, elastase, albumin, a-fetoprotein, and insulin). Typically, however, one will use an enhancer from a eukaryotic cellvirus. Examples include the SV40 enhancer on the late side of the replication origin (bp 100–270), the cytomegalovirus early promoter enhancer, the polyoma enhancer on the late side of the replication origin, and adenovirus enhancers. See also Yaniv, *Nature*, 297:17–18 (1982) on enhancing elements for activation of eukaryotic promoters. The enhancer may be spliced into the vector at a position 5' or 3' to the mpl ligand encoding sequence, but is preferably located at a site 5' from the promoter.

(vi) Transcription Termination Component

Expression vectors used in eukaryotic host cells (yeast, fungi, insect, plant, animal, human, or nucleated cells from other multicellular organisms) will also contain sequences necessary for the termination of transcription and for stabilizing the mRNA. Such sequences are commonly available from the 5' and, occasionally 3' untranslated regions of eukaryotic or viral DNAs or cDNAs. These regions contain nucleotide segments transcribed as polyadenylated fragments in the untranslated portion of the mRNA encoding mpl ligand.

(vii) Construction and Analysis of Vectors

Construction of suitable vectors containing one or more of the above listed components employs standard ligation techniques. Isolated plasmids or DNA fragments are cleaved, tailored, and religated in the form desired to generate the plasmids required.

For analysis to confirm correct sequences in plasmids constructed, the ligation mixtures are used to transform *E. coli* K12 strain 294 (ATCC 31,446) and successful transformants selected by ampicillin or tetracycline resistance where appropriate. Plasmids from the transformants are prepared, analyzed by restriction endonuclease digestion, and/or sequenced by the method of Messing et al., *Nucleic Acids Res.,* 9:309 (1981) or by the method of Maxam et al., *Methods in Enzymology,* 65:499 (1980).

(viii) Transient Expression Vectors

Particularly useful in the practice of this invention are expression vectors that provide for the transient expression in mammalian cells of DNA encoding the mpl ligand polypeptide. In general, transient expression involves the use of an expression vector that is able to replicate efficiently in a host cell, such that the host cell accumulates many copies of the expression vector and, in turn, synthesizes high levels of a desired polypeptide encoded by the expression vector. Sambrook et al., supra, pp. 16.17–16.22. Transient expression systems, comprising a suitable expression vector and a host cell, allow for the convenient positive identification of polypeptides encoded by cloned DNAs, as well as for the rapid screening of such polypeptides for desired biological or physiological properties. Thus, transient expression systems are particularly useful in the invention for purposes of identifying analogs and variants of mpl ligand polypeptide that have mpl ligand polypeptide biological activity.

(ix) Suitable Exemplary Vertebrate Cell Vectors

Other methods, vectors, and host cells suitable for adaptation to the synthesis of mpl ligand in recombinant vertebrate cell culture are described in Gething et al., *Nature,* 293: 620–625 [1981]; Mantei et al., *Nature,* 281:40–46 [1979]; Levinson et al.; EP 117,060; and EP 117,058. A particularly useful plasmid for mammalian cell culture expression of mpl ligand is pRK5 (EP pub. no. 307,247) or pSVI6B (U.S. Ser. No. 30 07/441,574 filed Nov. 22, 1989, the disclosure of which is incorporated herein by reference).

D. Selection and Transformation of Host Cells

Suitable host cells for cloning or expressing the vectors here in are the prokaryote, yeast, or higher eukaryotic cells described above. Suitable prokaryotes include eubacteria, such as Gram-negative or Gram-positive organisms, for example, *E. coli,* Bacilli such as *B. subtilis,* Pseudomonas species such as *P. aeruginosa, Salmonella typhimurium,* or *Serratia marcescans.* One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting. Preferably the host cell should secrete minimal amounts of proteolytic enzymes. Alternatively, in vitro methods of cloning, e.g., PCR or other nucleic acid polymerase reactions, are suitable.

In addition to prokaryptes, eukaryotic microbes such as filamentous fungi or yeast are suitable hosts for mpl ligand encoding vectors. *Saccharomyces cerevisiae,* or common baker's yeast, is the most commonly used among lower eukaryotic host microorganisms. However, a number of other genera, species, and strains are commonly available and useful herein, such as *Schizosaccharomyces pombe* [Beach and Nurse, *Nature,* 290:140 (1981); EP 139,383 published May 2, 1985], Kluyveromyces hosts (U.S. Pat. No. 4,943,529) such as, e.g., *K. lactis* [Louvencourt et al., *J. Bacteriol.,* 737 (1983)], *K. fragilis, K. bulgaricus, K. thermotolerans,* and *K. marxianus, yarrowia* [EP 402,226], *Pichia pastoris* [EP 183,070; Sreekrishna et al., *J. Basic Microbiol.,* 28:265–278 (1988)], *Candida, Trichoderma reesia* [EP 244,234], *Neurospora crassa* [Case et al., *Proc. Natl. Acad. Sci. USA,* 76:5259–5263 (1979)], and filamentous fungi such as, e.g., Neurospora, Penicillium, Tolypocladium [WO 91/00357 published Jan. 10, 1991], and Aspergillus hosts such as *A. nidulans* [Ballance et al., *Biochem. Biophys. Res. Commun.,* 112: 284–289 (1983); Tilbum, et al., *Gene,* 26:205–221 (1983); Yelton et al., *Proc. Natl. Acad. Sci. USA,* 81:1470–1474 (1984)] and *A. niger* [Kelly and Hynes, *EMBO J.,* 4: 475–479(1985)].

Suitable host cells for the expression of glycosylated mpl ligand are derived from multicellular organisms. Such host cells are capable of complex processing and glycosylation activities. In principle, any higher eukaryotic cell culture is workable, whether from vertebrate or invertebrate culture. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. See, e.g., Luckow et al., *Bio/Technology,* 6:47–55 (1988); Miller et al., in *Genetic. Engineering,* Setlow, J. K. et al., eds., Vol. 8 (Plenum Publishing, 1986), pp. 277–279; and Maeda et al., *Nature,* 315: 592–594 (1985). A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, petunia, tomato, and tobacco can be utilized as hosts. Typically, plant cells are transfected by incubation with certain strains of the bacterium *Agrobacterium tumefaciens,* which has been previously manipulated to contain the mpl ligand DNA. During incubation of the plant cell culture with *A. tumefaciens,* the DNA encoding the mpl ligand is transferred to the plant cell host such that it is transfected, and will, under appropriate conditions, express the mpl ligand DNA. In addition, regulatory and signal sequences compatible with plant cells are available, such as the nopaline synthase promoter and polyadenylation signal sequences. Depicker et al., *J. Mol. Appl. Gen.,* 1:561 (1982). In addition, DNA segments isolated from the upstream region of the T-DNA 780 gene are capable of activating or increasing transcription levels of plant-expressible genes in recombinant DNA-containing plant tissue. EP 321,196 published Jun. 21, 1989.

However, interest has been greatest in vertebrate cells, and propagation of vertebrate cells in culture (tissue culture) has become a routine procedure in recent years [Tissue Culture, Academic Press, Kruse and Patterson, editors (1973)]. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al. J. Gen Virol., 36:59 [1977]); baby hamster kidney cells (BHK, ATCC CCL 10); Chinese hamster ovary cells/- DHFR (CHO, Urlaub and Chasin, Proc. Natl. Acad. Sci. USA, 77:4216 [1980]); mouse sertoli cells (TM4, Mather, Biol. Reprod., 23:243–251 [1980];); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383: 44–68 [1982]); MRC 5 cells; FS4 cells; and a human hepatoma line (Hep G2).

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequences are in fact expressed. Numerous methods of transfection are known to the ordinarily skilled artisan, for example, $CaPO_4$ and electroporation. Successful transfection is generally recognized when any indication of the operation of this vector occurs within the host cell.

Transformation means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described in section 1.82 of Sambrook et al., supra, is generally used for prokaryotes or other cells that contain substantial cell-wall barriers. Infection with Agrobacterium tumefaciens is used for transformation of certain plant cells, as described by Shaw et al., Gene, 23: 315 (1983) and WO 89/05859 published Jun. 29, 1989. In addition, plants may be transfected using ultrasound treatment as described in WO 91/00358 published Jan. 10, 1991. For mammalian cells without such cell walls, the calcium phosphate precipitation method of Graham and van der Eb, Virology, 52:456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells such as by nuclear injection, electroporation, or protoplast fusion may also be used.

E. Culturing the Host Cells

Prokaryotic cells used to produce the mpl ligand polypeptide of this invention are cultured in suitable media as described generally in Sambrook et al., supra.

The mammalian host cells used to produce the mpl ligand of this invention may be cultured in a variety of media. Commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing the host cells. In addition, any of the media described in Ham and Wallace, Meth. Enz., 58: 44 (1979), Barnes and Sato, Anal. Biochem., 102:255 (1980), U.S. Pat. Nos. 4,767,704; 4,657,866; 4,927,762; or U.S. Pat. No. 4,560,655; WO 90/03430; WO 87/00195; U.S. Pat. Re. No. 30 30,985; or copending U.S. Ser. No. 07/592,107 or Ser. No. 07/592,141, both filed in Oct. 3, 1990, the disclosures of all of which are incorporated herein by reference, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

The host cells referred to in this disclosure encompass cells in in vitro culture as well as cells that are within a host animal.

F. Detecting Gene Amplification/Expression

Gene amplification and/or expression may be measured in a sample directly, for example, by conventional Southern blotting, northern blotting to quantitate the transcription of mRNA (Thomas, Proc. Natl. Acad. Sci. USA, 77:5201–5205 (1980]), dot blotting (DNA analysis), or in situ hybridization, using an appropriately labeled probe, based on the sequences provided herein. Various labels may be employed, most commonly radioisotopes, particularly $^{32}P$. However, other techniques may also be employed, such as using biotin-modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed that can recognize specific duplexes, including DNA duplexes, RNA duplexes, and DNA-RNA hybrid duplexes or DNA-protein duplexes. The antibodies in turn may be labeled and the assay may be carried out where the duplex is bound to a surface, so that upon the formation of duplex on the surface, the presence of antibody bound to the duplex can be detected.

Gene expression, alternatively, may be measured by immunological methods, such as immunohistochemical staining of tissue sections and assay of cell culture or body fluids, to quantitate directly the expression of gene product. With immunohistochemical staining techniques, a cell sample is prepared, typically by dehydration and fixation, followed by reaction with labeled antibodies specific for the gene product coupled, where the labels are usually visually detectable, such as enzymatic labels, fluorescent labels, luminescent labels, and the like. A particularly sensitive staining technique suitable for use in the present invention is described by Hsu et al., Am. J. Clin. Path., 75:734–738 (1980).

Antibodies useful for immunohistochemical staining and/ or assay of sample fluids may be either monoclonal or polyclonal, and may be prepared in any mammal.

Conveniently, the antibodies may be prepared against a native mpl ligand polypeptide or against a synthetic peptide based on the DNA sequences provided herein as described further below.

G. Purification of mpl Ligand Polypeptide

Mpl ligand preferably is recovered from the culture medium as a secreted polypeptide, although it also may be recovered from host cell lysates when directly expressed without a secretory signal.

When mpl ligand is expressed in a recombinant cell other than one of human origin, the mpl ligand is completely free of proteins or polypeptides of human origin. However, it is necessary to purify mpl ligand from recombinant cell proteins or polypeptides to obtain preparations that are substantially homogeneous as to mpl ligand. As a first step, the culture medium or lysate is centrifuged to remove particulate cell debris. The membrane and soluble protein fractions are then separated. The mpl ligand may then be purified from the soluble protein fraction and from the membrane fraction of the culture lysate, depending on whether the mpl ligand is membrane bound. Mpl ligand thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; ligand affinity chromatography, using, e.g., mpl and protein A Sepharose columns to remove contaminants such as IgG.

mpl ligand variants in which residues have been deleted, inserted, or substituted are recovered in the same fashion as native mpl ligand, taking account of any substantial changes in properties occasioned by the variation. For example, preparation of a mpl ligand fusion with another protein or polypeptide, e.g., a bacterial or viral antigen, facilitates purification; an immunoaffinity column containing antibody to the antigen can be used to adsorb the fusion polypeptide. Immunoaffinity columns such as a rabbit polyclonal anti-mpl ligand column can be employed to absorb the mpl ligand variant by binding it to at least one remaining immune epitope. Alternatively, the mpl ligand may be purified by affinity chromatography using a purified mpl-IgG coupled to a (preferably) immobilized resin such as Affi-Gel 10 (Bio-Rad, Richmond, Calif.) or the like, by means well known in the art. A protease inhibitor such as phenyl methyl sulfonyl fluoride (PMSF) also may be useful to inhibit proteolytic degradation during purification, and antibiotics may be included to prevent the growth of adventitious contaminants. One skilled in the art will appreciate that purification methods suitable for native mpl ligand may require modification to account for changes in the character of mpl ligand or its variants upon expression in recombinant cell culture.

H. Covalent Modifications of mpl Ligand Polypeptide

Covalent modifications of mpl ligand polypeptides are included within the scope of this invention. Both native mpl ligand and amino acid sequence variants of the mpl ligand may be covalently modified. One type of covalent modification included within the scope of this invention is a mpl ligand fragment. Variant mpl ligand fragments having up to about 40 amino acid residues may be conveniently prepared by chemical synthesis or by enzymatic or chemical cleavage of the full-length or variant mpl ligand polypeptide. Other types of covalent modifications of the mpl ligand or fragments thereof are introduced into the molecule by reacting targeted amino acid residues of the mpl ligand or fragments thereof with an organic derivatizing agent that is capable of reacting with selected side chains or the N- or C-terminal residues.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, a-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1M sodium cacodylate at pH 6.Q.

Lysinyl and amino terminal residues are reacted with succinic or other carboxylic acid anhydrides. Derivatization with these agents has the effect of reversing the charge of the lysinyl residues. Other suitable reagents for derivatizing a-amino-containing residues include imidbesters such as methyl picolinimidate; pyridoxal phosphate; pyridoxal; chlorobdrohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking mpl ligand to a water-insoluble support matrix or surface for use in the method for purifying anti-mpl ligand antibodies, and vice-versa. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio] propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. These residues are deamidated under neutral or basic conditions. The deamidated form of these residues falls within the scope of this invention.

Other modifications include hydroxylation of proline and lysine, phosphorylation of hydroxyl groups of seryl or threonyl residues, methylation of the a-amino groups of lysine, arginine, and histidine side chains (T. E. Creighton, *Proteins: Structure and Molecular Properties,* W. H. Freeman & Co., San Francisco, pp. 79–86 [1983]), acetylation of the N-terminal amine, and amidation of any C-terminal carboxyl group.

Another type of covalent modification of the mpl ligand polypeptide included within the scope of this invention comprises altering the native glycosylation pattern of the polypeptide. By altering is meant deleting one or more carbohydrate moieties found in native mpl ligand, and/or adding one or more glycosylation sites that are not present in the native mpl ligand.

Glycosylation of polypeptides is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the mpl ligand polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the native mpl ligand sequence (for O-linked glycosylation sites). For ease, the mpl ligand amino acid sequence is preferably altered through changes at the DNA level, particularly by mutating the DNA encoding the mpl ligand polypeptide at preselected bases such that codons are generated that will translate, into the desired amino acids. The DNA mutation(s) may be made using methods described above under the heading of "Amino Acid Sequence Variants of mpl ligand."

Another means of increasing the number of carbohydrate moieties on the mpl ligand is by chemical or enzymatic coupling of glycosides to the polypeptide. These procedures are advantageous in that they do not require production of the polypeptide in a host cell that has glycosylation capabilities for N- or O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330 published Sep. 11, 1987, and in Aplin and Wriston, *CRC Crit. Rev. Biochem.,* pp. 259–306 (1981).

Removal of carbohydrate moieties present on the mpl ligand polypeptide may be accomplished chemically or enzymatically. Chemical deglycosylation requires exposure of the polypeptide to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin, et al., *Arch. Biochem. Biophys.,* 259:52 (1987) and by Edge et al., *Anal. Biochem.,* 118:131 (1981). Enzymatic cleavage of carbohydrate moieties on polypeptides can be achieved by the use of a variety of endo- and exo-glycosidases as described by Thotakura et al., *Meth. Enzymol.,* 138:350 (1987).

Glycosylation at potential glycosylation sites may be prevented by the use of the compound tunicamycin as described by Duskin et al., *J. Biol. Chem.,* 257:3105 (1982). Tunicamycin blocks the formation of protein-N-glycoside linkages.

Another type of covalent modification of mpl ligand comprises linking the mpl ligand polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or U.S. Pat. No. 4,179,337.

It will be appreciated that some screening of the recovered mpl ligand variant will be needed to select the optimal variant for binding to a mpl and having the immunological and/or biological activity defined above. One can screen for stability in recombinant cell culture or in plasma (e.g., against proteolytic cleavage), high affinity to a mpl member, oxidative stability, ability to be secreted in elevated yields, and the like. For example, a change in the immunological character of the mpl ligand polypeptide, such as affinity for a given antibody, is measured by a competitive-type immunoassay. Other potential modifications of protein or polypeptide properties such as redox or thermal stability, hydrophobicity, or susceptibility to proteolytic degradation are assayed by methods well known in the art.

4. Preparation of Antibodies to the mpl Ligand

Polyclonal antibodies to the mpl ligand polypeptide generally are raised in animals by multiple subcutaneous (sc) or intraperitoneal (ip) injections of the mpl ligand polypeptide and an adjuvant. It may be useful to conjugate the mpl ligand polypeptide (including fragments containing a specific amino acid sequence) to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

The route and schedule of immunizing a host animal or removing and culturing antibody-producing cells are generally in keeping with established and conventional techniques for antibody stimulation and production. While mice are frequently employed as the host animal, it is contemplated that any mammalian subject including human subjects or antibody-producing cells obtained therefrom can be manipulated according to the processes of this invention to serve as the basis for production of mammalian, including human, hybrid cell lines.

Animals are typically immunized against the immunogenic conjugates or derivatives by combining 1 mg or 1 μg of mpl ligand conjugate (for rabbits or mice, respectively) with 3 volumes of Freund's complete adjuvant and injecting the solution intradermally at multiple sites. One month later the animals are boosted with ⅕ to ⅒ the original amount of conjugate in Freund's complete adjuvant (or other suitable adjuvant) by subcutaneous injection at multiple sites. Seven to 14 days later animals are bled and the serum is assayed for anti-mpl ligand polypeptide titer. Animals are boosted until the titer plateaus. Preferably, the animal is boosted with the conjugate of the same mpl ligand polypeptide, but conjugated to a different protein and/or through a different cross-linking agent. Conjugates also can be made in recombinant cell culture as protein fusions. Also, aggregating agents such as alum are used to enhance the immune response.

Monoclonal antibodies are prepared by recovering immune cells—typically spleen cells or lymphocytes from lymph node tissue—from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, *Eur. J. Immunol.,* 6:511 (1976) and also described by Hammerling et al., In: *Monoclonal Antibodies and T-Cell Hybridomas,* Elsevier, N.Y., pp. 563–681 (1981) has been widely applied to produce hybrid cell lines that secrete high levels of monoclonal antibodies against many specific antigens.

It is possible to fuse cells of one species with another. However, it is preferable that the source of the immunized antibody-producing cells and the myeloma be from the same species.

The hybrid cell lines can be maintained in culture in vitro in cell culture media. The cell lines of this invention can be selected and/or maintained in a composition comprising the continuous cell line in hypoxanthine-aminopterin thymidine (HAT) medium. In fact, once the hybridoma cell line is established, it can be maintained on a variety of nutritionally adequate media. Moreover, the hybrid cell lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant by conventional methods such as precipitation, ion exchange chromatography, affinity chromatography, or the like. The antibodies described herein are also recovered from hybridoma cell cultures by conventional methods for purification of IgG or IgM, as the case may be, that heretofore have been used to purify these immunoglobulins from pooled plasma, e.g., ethanol or polyethylene glycol precipitation procedures. The purified antibodies are sterile filtered, and optionally are conjugated to a detectable marker such as an enzyme or spin label for use in diagnostic assays of the mpl ligand in test samples.

While routinely mouse monoclonal antibodies are used, the invention is not so limited; in fact, human antibodies may be used and may prove to be preferable. Such antibodies can be obtained by using human hybridomas (Cote et al., *Monoclonal Antibodies and Cancer Therapy,* Alan R. Liss, p. 77 [1985]). In fact, according to the invention, techniques developed for the production of chimeric antibodies (Morrison et al., *Proc. Natl. Acad. Sci.,* 81:6851 [1984]; Neuberger et al., *Nature,* 312:604 [1984]; Takeda et al., *Nature,* 314:452 [1985]; EP 184,187; EP 171,496; EP 173, 494; PCT WO 86/01533; Shaw et al., *J. Nat. Canc. Inst.,* 80:1553–1559 [1988]; Morrison, *Science,* 229:1202–1207 [1985]; and Oi et al., *Bio Techniques,* 4:214 [1986]) by splicing the genes from a mouse antibody molecule of appropriate antigen specificity together with genes from a human antibody molecule of appropriate biological activity (such as ability to activate human complement and mediate ADCC) can be used; such antibodies are within the scope of this invention.

Techniques for creating recombinant DNA versions of the antigen-binding regions of antibody molecules (known as Fab fragments), which bypass the generation of monoclonal antibodies, are encompassed within the practice of this invention. One extracts antibody-specific messenger RNA molecules from immune system cells taken from an immunized animal, transcribes these into complementary DNA (cDNA), and clones the cDNA into a bacterial expression system. One example of such a technique suitable for the practice of this invention was developed by researchers at Scripps/Stratagene, and incorporates a proprietary bacteriophage lambda vector system that contains a leader sequence that causes the expressed Fab protein to migrate to the periplasmic space (between the bacterial cell membrane and the cell wall) or to be secreted. One can rapidly generate and screen great numbers of functional Fab fragments for those that bind the antigen. Such mpl ligand-binding molecules (Fab fragments with specificity for the mpl ligand polypeptide) are specifically encompassed within the term "antibody" as it is defined, discussed, and claimed herein.

IV. Therapeutic Use of the Megakaryocytopoietic Protein

The biologically active mpl ligand having hematopoetic effector function and referred to here as a megakaryocytopoietic protein may be used in a sterile pharmaceutical preparation or formulation to stimulate thrombopoeitic activity in patients suffering from thrombocytopenia due to impaired production, sequestration, or increased destruction of platelets. Thombocytopenias associated bone marrow hypoplasia (e.g., aplastic anemia following chemotherapy or bone marrow transplant) may be effectively treated with the compounds of this invention as well as disorders such as disseminated intravascular coagulation (DIC), immune thrombocytopenia (including HIV-induced ITP and non HIV-induced ITP) and thrombotic thrombocytopenia. Additionally, these megakaryocyteopoeitic proteins may be useful in treating meyloproliferative thrombocytotic diseases as well as thrombocytosis from inflammatory conditions and in iron deficiency.

Still other disorders usefully treated with the megakaryocyteopoeitic proteins of this invention include defects or damage to platelets resulting from drugs, poisoning or activation on artificial surfaces. In these cases, the instant compounds may be employed to stimulate "shedding" of, new "undamaged" platelets. For a more complete list of useful applications, see the "Background" supra, especially section (a)–(f) and references cited therein.

The megakaryocyteopoeitic proteins of the instant invention may be employed alone or in combination with other cytokines, hematopoietins, interleukins, growth factors, or antibodies in the treatment of the above-identified disorders and conditions. Thus, the instant compounds may be employed in combination with other protein or peptide having thrombopoeitic activity including; G-CSF, CSF-1, GM-CSF, M-CSF, IL-1, IL-3, IL-4, IL-5, erythropoietin (EPO), IL-6, IL-7, and IL-8.

The megakaryocyteopoeitic proteins of the instant invention are prepared in a mixture with a pharmaceutically acceptable carrier. This therapeutic composition can be administered orally, intravenously or through the nose or lung. The composition may also be administered parenterally or subcutaneously as desired. When administered systematically, the therapeutic composition should be pyrogen-free and in a parenterally acceptable solution having due regard for pH, isotonicity, and stability. These conditions are known to those skilled in the art. Briefly, dosage formulations of the compounds of the present invention are prepared for storage or administration by mixing the compound having the desired degree of purity with physiologically acceptable carriers, excipients, or stabilizers. Such materials are non-toxic to the recipients at the dosages and concentrations employed, and include buffers such as phosphate, citrate, acetate and other organic acid salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino acids such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

About 0.5 to 500 mg of a compound or mixture of the megakaryocyteopoeitic protein as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixer may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

Suitable examples of sustained-release preparations include semipermeable matrices of solid hydrophobic polymers containing the polypeptide, which matrices are in the form of shaped articles, e.g., films, or microcapsules. Examples of sustained-release matrices include polyesters, hydrogels [e.g., poly(2-hydroxyethyl-methacrylate) as described by Langer et al., *J. Biomed. Mater. Res.*, 15:167–277 [1981] and Langer, *Chem. Tech.*, 12:98–105 [1982] or poly(vinylalcohol)], polylactides (U.S. Pat. No. 3,773,919, EP 58,481), copolymers of L-glutamic acid and gamma ethyl-L-glutamate (Sidman et al., *Biopolymers*, 22:547–556 [1983]), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(−)-3-hydroxybutyric acid (EP 133,988).

While polymers such as ethylene-vinyl acetate and lactic acid-glycolic acid enable release of molecules for over 100 days, certain hydrogels release proteins for shorter time periods. When encapsulated proteins remain in the body for a long time, they may denature or aggregate as a result of exposure to moisture at 37° C., resulting in a loss of biological activity and possible changes in immunogenicity. Rational strategies can be devised for protein stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Sustained-release megakaryocyteopoeitic protein compositions also include liposomally entrapped megakaryocyteopoeitic protein. Liposomes containing megakaryocyteopoeitic protein are prepared by methods known per se: DE 3,218,121; Epstein et al., *Proc. Natl. Acad. Sci. USA*, 82:3688–3692 (1985); Hwang et al., *Proc. Natl. Acad. Sci. USA*, 77:4030–4034 (1980); EP 52,322; EP 36,676; EP 88,046; EP 143,949; EP 142,641; Japanese patent application 83-118008; U.S. Pat. Nos. 4,485,045 and 4,544,545; and EP 102,324. Ordinarily the lipbsomes are of the small (about 200–800 Angstroms) unilamellar type in which the lipid content is greater than about 30 mol. % cholesterol, the selected proportion being adjusted for the optimal megaokarycyteopoeitic protein therapy.

The dosage will be determined by the attending physician taking into consideration various factors known to modify the action of drugs including severity and type of disease, body weight, sex, diet, time and route of administration, other medications and other relevant clinical factors. Typically, the daily regimen will range from 1–3000 μg/kg body weight. Preferably the dosage will range from 10–1000 μg/kg body weight. Most preferably, the dosage will range from 50 to 150 mg/day. Therapeutically effective dosages may be determined by either in vitro or in vivo methods.

EXAMPLES

Without further description, it is believed that one of ordinary skill in the art can, using the preceding description and illustrative examples, make and utilize the present invention to the fullest extent. The following working examples therefore specifically point out preferred embodiments of the present invention, and are not to be construed as limiting in any way of the remainder of the disclosure.

Example I

Partial Purification of the MPL-ligand

Aplastic porcine plasma obtained from irradiated pigs is made 4M with NaCl and stirred for 30 min. at room temperature. The resultant precipitate is removed by centrifugation at 3800 rpm in a Sorvall RC3B and the supernatant is loaded onto a Phenyl-Toyopearl column equilibrated in 10 mM $NaPO_4$ containing 4M NaCl. The column is washed with this buffer until $A_{280}$ is <0.05 and eluted with $dH_2O$. The eluted protein peak is diluted with $dH_2O$ to a conductivity of 15 mS and loaded onto a Blue-Sepharose column equilibrated in PBS. Subsequently, the column is washed with 5 column volumes each of PBS and 10 mM $NaPO_4$ (pH 7.4) containing 2M urea. Proteins are eluted from the column with 10 mM $NaPO_4$ (pH 7.4) containing 2M urea and 1M NaCl. The eluted protein peak is made 0.01% octyl glucoside(n-octyl β-D-glucopyranoside) and 1 mM each with EDTA and Pefabloc and loaded directly onto tandemly linked CD4-IgG and mpl-IgG ultralink (Pierce) columns (see below). The CD4-IgG column is removed after the sample is loaded and the mpl-IgG column is washed with 10 column volumes each of PBS and PBS containing 2 M NaCl and eluted with 0.1M glycine-HCL pH 2.25. Fractions are collected into 1/10th volume 1M tris pH 8.0.

Analysis of eluted fractions from the mpl-affinity column by SDS-PAGE (4–20%, novex gel) run under reducing conditions, reveal the presence of several proteins (FIG. 3). Proteins that silver stain with the strongest intensity resolve with apparent Mr of 66,000, 55,000, 30,000, 28,000 and 14,000. To determine which of these proteins stimulate proliferation Ba/F3-mpl cell cultures these proteins were eluted from the gel as described in a Example II below.

Ultralink Affinity Columns 1.0–20 mg of mpl-IgG or CD4-IgG in PBS are coupled to 0.5 grams of Ultralink resin (Pierce) as described by the manufactures instructions.

Construction and Expression of mpl-IgG

A chimeric molecule comprising the entire extracelluar domain of human mpl P (amino acids 1–491) and the Fc region of a human IgG1 molecule was expressed in 293 cells. A cDNA fragment corresponding to amino acids 1–491 of human mpl P was obtained by PCR from a human platelet cDNA library. A ClaI site was inserted at the 5' end and a BstEII site at the 3' end. The fragment was cloned upstream of the IgGI Fc region in a Bluescript vector between the ClaI and. the BstEII sites after partial digestion of the PCR product with BstEII because of 2 other BstEII sites present in the extracellular domain of mpl. The BstEII site introduced at the 3' end of the mpl PCR product was designed to have the Fc region in frame with the mpl extracellular domain. The construct was subcloned into pRK5-tkneo vector between the ClaI and XbaI sites and transfected into 293 human embryonic kidney cells by the calcium phosphate method. The cells were selected in 0.4 mg/ml G418 and individual clones were isolated. mpl-IgG expression from isolated clones was determined using a human Fc specific ELISA. One clone had the highest expression of 1–2 mg/ml.

Example II

Highly Purified mpl Ligand

Gel Elution Protocol

Equal amounts of affinity purified mpl ligand (fraction 6 eluted from the mpl-IgG column) and 2× Laemmli sample buffer were mixed at room temperature without reducing agent and loaded onto a Novex 4–20% polyacrylamide gel as quickly as possible. The sample was not heated. As a control, sample buffer without ligand was run in an adjacent lane. The gel was run at 4–6 C. at 135 volts for approximately 2¼ hours. The running buffer was initially at room temperature. The gel was then removed from the gel box and the plate on one side of the gel removed.

A replica of the gel was made on nitrocellulose as follows: A piece of nitrocellulose was wet with distilled water and carefully laid on top of the exposed gel face so air bubbles were excluded. Fiducial marks were placed on the nitrocellulose and the gel plate so the replica could be accurately repositioned after staining. After approximately 2 minutes, the nitrocellulose was carefully removed, and the gel was wrapped in plastic wrap and placed in the refrigerator. The nitrocellulose was stained with Biorad's gold total protein stain by first agitating it. in 3×10 mL 0.1% Tween 20+0.5 M NaCl+0.1 M Tris-HCl pH 7.5 over approximately 45 minutes followed by 3×10 mL purified water over 5 minutes.

The gold stain was then added and allowed to develop until the bands in the standards were visible. The replica was then rinsed with water, placed over the plastic wrap on the gel and carefully aligned with the fiducial marks. The positions of the Novex standards were marked on the gel plate and lines were drawn to indicate the cutting positions. The nitrocellulose and plastic wrap were then removed and the gel cut along the indicated lines with a sharp razor blade. The cuts were extended beyond the sample lanes so they could be used to determine the positions of the slices when the gel was stained. After the slices were removed, the remaining gel was silver stained and the positions of the standards and the cut marks measured. The molecular weights corresponding to the cut positions were determined from the Novex standards.

The 12 gel slices were placed into the cells in two Biorad model 422 electro-eluters. 12–14K molecular weight cutoff membrane caps were used in the cells. 50 mM ammonium bicarbonate+0.05% SDS (approximately pH 7.8) was the elution buffer. 1 L of buffer was chilled approximately 1 hour in a 4–6 C. coldroom before use. Gel slices were eluted at 10 ma/cell (40 v initially) in a 4–6 C. coldroom. Elution took approximately 4 hours. The cells were then carefully removed and the liquid above the frit removed with a pipet. The elution chamber was removed and any liquid above the membrane cap removed with a pipet. The liquid in the membrane cap was removed with a Pipetman and saved. 50 uL aliquots of purified water were then placed in the cap, agitated and removed until all the SDS crystals dissolved. These washes were combined with the saved liquid above. Total elution sample volume was 300–500 uL per gel slice. Samples were placed in 10 mm Spectrapor 4 12–14K cutoff dialysis tubing which had been soaked several hours in purified water. They were dialyzed overnight at 4–6 C. against 600 mL of phosphate buffered saline (PBS is approximately 4 mM in potassium) per 6 samples. The buffer was replaced the next morning and dialysis continued for 2.5 hours. Samples were then removed from the dialysis bags and placed in microfuge tubes. The tubes were placed on ice for 1 hour, microfuged at 14K rpm for 3 min. and the supernantants carefully removed from the precipitated SDS. The supernatants were then placed on ice for approximately 1 hour more and microfuged again for 4 min. The supernatants were diluted in phosphate buffered saline and submitted for the activity assay. Remaining samples were frozen at −70 C.

Example III

Mpl Ligand Microsequencing

Fraction 6 (2.6 ml) from the MPL-IgG affinity column was concentrated on a Microcon-10 (Amicon). In order to prevent the MPL ligand from absorbing to the Microcon, the membrane was rinsed with 1% SDS and 5 μl of 10% SDS was added to fraction 6. Sample buffer (20 μl) of 2× was added to the fraction #6 after Microcon concentration (20 μl) and the total volume (40 μl) was loaded on a single lane of a 4–20% gradient acrylamide gel (Novex). The gel was run following Novex protocol. The gel was then equilibrated for 5 min. prior to electroblotting in 10 mM 3-(cyclohexylamino)-1-propanesulfonic acid (CAPS) buffer, pH 11.0, containing 10% methanol. Electroblotting onto Immobilon-PSQ membranes (Millipore) was carried out for 45 min. at 250 mA constant current in a BioRad Trans-Blot transfer cell (32). The PVDF membrane was stained with 0.1% Coomassie Blue R-250 in 40% methanol, 0.1% acetic acid for 1 min. and destained for 2–3 min. with 10% acetic acid in 50% methanol. The only proteins that were visable in the Mr 18,000–35,000 region of the blot had Mr of 30,000, 28,000 and 22,000.

Bands at 30, 28 and 22 KDa were subjected to protein sequencing. Automated protein sequencing was performed on a model 470A Applied Biosystem sequencer equipped with an on-line PTH analyzer. The sequencer was modified to inject 80–90% of the sample (Rodriguez, H. *J. Chromatogr.* 350:217–225 [1985]). Acetone (~12 μl/L) was added to solvent A to balance the UV absorbance. Electroblotted proteins were sequenced in the Blott cartridge. Peaks were integrated with Justice Innovation software using Nelson Analytical 970 interfaces. Sequence interpretation was performed on a VAX 5900 (Henzel, W. J., Rodriguez, H., and Watanabe, C. *J. Chromatogr.* 404:41–52 [i987]). N-terminal sequence using one letter code with uncertain residues in parenthesis of indicated gel bands were:

```
1) 30 KDa (1.8 pmol)
   1        5         10        15        20        25
  (S) P A P P A(C)D P R L L N K L L R D D (H/S) V L H (G) R L (SEQ ID NO.:3)

2) 28 KDa (0.5 pmol)
   1        5         10        15        20        25
  (S) P A P P A X D P R L L N K L L R D D (H) V L (H) G R (SEQ ID NO.:4)

3) 22 KDa (0.5 pmol)
   1        5         10
   X P A P P A X D P R L X (N) (K) (SEQ ID NO.:5)
```

Example IV
Liquid Suspension Megakaryocytopoiesis Assay

Human peripheral stem cells (PSC) (obtained from consenting patients) were diluted 5 fold with IMDM media (Gibco) and centrifuged for 15 min. at room temp. at 800×g. The cell pellets were resuspended in IMDM and layered onto 60% percoll (density 1.077 gm/ml ) (Pharmacia) and centrifuged at 800×g for 30 min. The light density mononuclear cells were aspirated at the interface and washed 2× with IMDM and plated out at 1–2×10⁶ cells/ml in IMDM containing 30% FBS (1 ml final volume) in 24 well tissue culture clusters (Costar). APP or mpl-ligand depleted APP was added to 10% and cultures were grown for 12–14 days in a humidified incubator at 37 C. in 5% $CO_2$ and air, The cultures were also grown in the presence of 10% APP with 0.5 μg of mpl-IgG added at days 0, 2 and 4. APP was depleted of mpl-ligand by passing APP through a mpl-IgG affinity column.

To quanitate megakaryocytopoiesis in these liquid suspension cultures, a modification of (Solberg, L. A. et al. ) was used and employs a radiolabled murine IgG monoclonal antibody (HP1-1D) to GPIIbIIIa (provided by Dr. Nichols-, Mayo Clinic)-. 100 μg of HP1-1D was radiolabled with 1mCi of $Na^{125}I$ using enzymobeads (Biorad, Richmond Calif.) as described by the manufactures instructions. Radiolabled HP1-1D was stored at −70° C. in PBS containing 0.01% octyl-glucoside. Typical specific activities were 1–2× 10⁶ cpm/μg (>95% precipital by 12.5% trichloroacetic acid).

Liquid suspension cultures were set up in triplicate for each experimental point. After 12–14 days in culture the 1 ml cultures were transferred to 1.5 ml eppendorf tubes and centrifuged at 800×g for 10 min. at room temp. and the resultant cell pellets were resuspended in 100 μl of PBS containing 0.02% EDTA and 20% bovine calf serum. 10 ng of $^{125}I$-HP1-1D in 50 μl of assay buffer was added to the resuspended cultures and incubated for 60 min. at RT with occasional shaking. Subsequently, cells were collected by centrifugation at 800×g for 10 min at RT and washed 2× with assay buffer. The pellets were counted for 1 min. in a gamma counter (Packard). Non-specific binding was determined by adding 1 ug of unlabled HP1-1D for 60 min. before the addition of labeled HP1-1D. Specific binding was determined as the total $^{125}I$-HP1-1 D bound minus that bound in the presence of excess unlabled HP1-1D.

Example V
Oligonucleotide PCR Primers

Based on the amino-terminal amino acid sequence obtained from the 30 kDa, 28 kDa and 22 kDa proteins, degenerate oligonucleotides were designed for use as polymerase chain reaction (PCR) primers. Two primer pools were synthesized, a positive sense 20 mer pool encoding amino acid residues 2–8 (mpl.1) and a negative sense 21 mer pool encoding amino acids 18–24 (mpl. 2).

mpl. 1 5' CCN GCN CCN CCN GCN TGY GA 3' (SEQ ID NO.: 6) (2,048-fold degenerate)

mpl. 2 5' NCC RTG NAR NAC RTG RTC RTC 3' (SEQ ID NO.: 7) (2,048-fold degenerate)

Porcine genomic DNA, isolated from porcine peripheral blood lymphocytes, was used as a template for PCR. The 50 μl reaction contained: 0.8 μg of porcine genomic DNA in 10 mM Tris pH 8.3, 50 mM KCl, 3 mM $MgCl_2$, 100 ug/ml BSA, 400 μM dNTPs, 1 μM of each primer pool and 2.5 units of Taq polymerase. Initial template denaturation was at 94° C. for 8 min. followed by 35 cycles of 45 seconds at 94° C., 1 min. at 55° C. and 1 min. at 72° C. The final cycle was allowed to extend for 10 min. at 72° C. PCR products were separated by electrophoresis on a 12% polyacrylamide gel and visualized by staining with ethidium bromide. If the amino-terminal amino acid sequence is encoded by a single exon then the correct PCR product is expected to be 69 bp. A DNA fragment of this size was eluted from the gel and subcloned into pGEMT (Promega). Sequences of three clones are shown below:

(1) gemT3

5' CCAGCGCCGC CAGCCTGTGA CCCCCGACTC CTAAATAAAC TGCCTCGTGA
3' GGTCGCGGCG GTCGGACACT GGGGGCTGAG GATTTATTTG ACGGAGCACT
TGACCACGTT CAGCACGGC 3' (SEQ ID NO.: 8) 69
ACTGGTGCAA GTCGTGCCG 5'

(2) gemT7

5' CCAGCACCTC CGGCATGTGA CCCCCGACTC CTAAATAAAC TGCTTCGTGA
3' GGTCGTGGAG GCCGTACACT GGGGGCTGAG GATTTATTTG ACGAAGCACT
CGACCACGTC CATCACGGC 3' (SEQ ID NO.: 9) 69
GCTGGTGCAG GTAGTGCCG 5'

(3) gemT9

```
              P  R  L  L  N  K  L  L  R
5' CCAGCACCGCCGGCATGTGACCCCCGACTCCTAAATAAACTGCTTCGTGACG   (SEQ ID NO.: 10)
3' GGTCGTGGCGGCCGTACACTGGGGGCTGAGGATTTATTTGACGAAGCACTGC
```

```
ATCATGTCTATCACGGT 3'                                      (SEQ ID NO.: 11)
TAGTACAGATAGTGCCA 5'
```

The position of the PCR primers is indicated by the underlined bases. These results verify the N-terminal sequence obtained for amino acids 9–17 for the 30 kDa, 28 KDa and 22 kDa proteins and indicated that this sequence is encoded by a single exon of porcine DNA.

Based on these results a single oligonucleotide of 53 nucleotides was synthesized (from AA position 2 to 19), labeled with $^{32}$P and used to screen porcine and human genomic DNA libraries in order to isolate the porcine and human mpl ligand genes. This "consensus probe" has the following sequence:

5' CCA GCA CCG CCG GCA TGT GAC CCC CGA CTC CTA AAT AAA CTG CTT CGT GAC GA 3' (SEQ ID NO.: 12)

Example VI
CMK Assay for Thrombopoletin (TPO) Induction of Platelet Antigen GPII$_b$III$_a$ Expression CMK cells are maintained in RMPI 1640 medium (Sigma) supplemented with 10% fetal bovine serum and 10 mM glutamine. In preparation for the assay, the cells are harvested, washed and resuspended at 5×10$^5$ cells/ml in serum-free GIF medium supplemented with 5 mg/L bovine insulin, 10 mg/L apo-transferrin, 1× trace elements. In a 96-well flat-bottom plate, the TPO standard or experimental samples are added to each well at appropriate dilutions in 100 ul volumes. 100 ul of the CMK cell suspension is added to each well and the plates are incubated at 37° C., in a 5% CO$_2$ incubator for 48 hours. After incubation, the plates are spun at 1000 rpm at 4° C. for five minutes. Supernatants are discarded and 100 ul of the FITC-conjugated GPII$_b$III$_a$ monoclonal 2D2 antibody is added to each well. Following incubation at 4° C. for 1 hour, plates are spun again at 1000 rpm for five minutes. The supernatants containing unbound antibody are discarded and 200 ul of 0.1% BSA-PBS wash is added to each well. The 0.1% BSA-PBS wash step is repeated three times. Cells are then analyzed on a FASCAN using standard one parameter analysis measuring relative fluorescence intensity.

Example VII
DAMI Assay for Thrombopoietin (TPO) by Measuring Endomitotic Activity of DAMI Cells on 96-well Microtiter Plates DAMI cells are maintained in IMDM+10% horse serum (Gibco) supplemented with 10 mM glutamine, 10 ng/ml Penicillin G, and 50 ug/ml streptomycin. In preparation for the assay, the cells are harvested, washed, and resuspended at 1×10$^6$ cells/ml in IMDM+1% horse serum. In a 96-well round-bottom plate, 100 ul of the TPO standard or experimental samples is added to DAMI cell suspension. Cells are then incubated for 48 hours at 37° in a 5% CO$_2$ incubator. After incubation, plates are spun in a Sorvall 6000B centrifuge at 1000 rpm for five minutes at 4° C. Supernatants are discarded and 200 ul of PBS-0.1% BSA wash step is repeated. Cells are fixed by the addition of 200 ul ice-cold 70% Ethanol-PBS and resuspended by aspiration. After incubation at 4° C. for 15 minutes, the plates are spun at 2000 rpm for five minutes and 150 ul of 1 mg/ml RNAse containing 0.1 mg/ml Propidium Iodide and 0.05% Tween-20 is added to each well. Following a one hour incubation at 37° C. the changes in DNA content are measured by flow cytometry. Polyploidy is measured and quantitated as follows:

$$\text{Normalized Polyploid Ratio (NPR)} = \frac{(\%\text{ Cells in} > G2 + M\, /\, \%\text{ Cells in} < G2 + M)\text{ with TPO}}{(\%\text{ Cells in} > G2 + M\, /\, \%\text{ Cells in} < G2 + M)\text{ in control}}$$

Example VIII

Thrombopoietin (TPO) in vivo Assay (Mouse Platelet Rebound Assay)

In vivo Assay for $^{35}$S Determination of Platelet Production

C57BL6 mice (obtained from Charles River) are injected intraperitoneally (IP) with 1 ml goat anti-mouse platelet serum (6 amps) on day 1 to produce thrombocytopenia. On days 5 and 6, mice are given two IP injections of the factor or PBS as the control. On day 7, thirty $\mu$Ci of Na$_2$$^{35}$SO$_4$ in 0.1 ml saline are injected intravenously and the percent $^{35}$S incorporation of the injected dose into circulating platelets is measured in blood samples obtained from treated and control mice. Platelet counts and leukocyte counts are made at the same time from blood obtained from the retro-orbital sinus.

While the invention has necessarily been described in conjunction with preferred embodiments and specific working examples, one of ordinary skill, after reading the foregoing specification, will be able to effect various changes, substitutions of equivalents, and alterations to the subject matter set forth herein, without departing from the spirit and scope thereof. Hence, the invention can be practiced in ways other than those specifically described herein. It is therefore intended that the protection granted by Letters Patent hereon be limited only by the appended claims and equivalents thereof.

All references cited herein are hereby expressly incorporated by reference.

We claim:

1. An isolated substantially homogeneous naturally occurring Porcine mpl ligand.

2. The isolated substantially homogeneous mpl ligand of claim 1 characterized in that:

(1) the ligand stimulates the incorporation of labeled nucleotides ($^3$H-thymidine) into the DNA of IL-3 dependant Ba/F3 cells transfected with human mpl P; and (2) the amino-terminal sequence is SPAPPACD-PRLLNKLLRDDHVLHGR (SEQ ID NO: 2).

3. A composition comprising the mpl ligand of claim 1 and a pharmaceutically acceptable carrier.

* * * * *